(12) United States Patent
Maseda et al.

(10) Patent No.: US 9,545,502 B2
(45) Date of Patent: Jan. 17, 2017

(54) CATHETER CONNECTION AND STABILIZATION DEVICE AND METHODS OF USING SAME

(71) Applicant: NP Medical Inc., Clinton, MA (US)

(72) Inventors: Luis Maseda, Natick, MA (US); Todd Chelak, Westborough, MA (US); Nicholas Dennis, Sterling, MA (US); Ian Kimball, Townsend, MA (US)

(73) Assignee: NP Medical Inc., Clinton, MA (US)

( * ) Notice: Subject to any disclaimer, the term of this patent is extended or adjusted under 35 U.S.C. 154(b) by 0 days.

(21) Appl. No.: 14/802,270

(22) Filed: Jul. 17, 2015

(65) Prior Publication Data

US 2015/0320976 A1    Nov. 12, 2015

Related U.S. Application Data

(63) Continuation-in-part of application No. 14/408,436, filed as application No. PCT/US2014/051217 on Aug. 15, 2014.

(Continued)

(51) Int. Cl.
*A61M 5/32* (2006.01)
*A61M 5/00* (2006.01)
(Continued)

(52) U.S. Cl.
CPC ............ *A61M 25/02* (2013.01); *A61M 39/12* (2013.01); *A61M 39/22* (2013.01); *A61M 39/24* (2013.01);
(Continued)

(58) Field of Classification Search
CPC ............ A61M 25/02; A61M 2025/0206; A61M 2025/0253; A61M 2025/0266; A61M 2025/0273; A61M 2025/028; A61M 39/12; A61M 39/24; A61M 2039/2406; A61M 2039/242; A61M 2039/2426
(Continued)

(56) References Cited

U.S. PATENT DOCUMENTS

| 5,354,282 | A | 10/1994 | Bierman | 604/180 |
| 5,707,348 | A | 1/1998 | Krogh | 602/41 |

(Continued)

FOREIGN PATENT DOCUMENTS

| EP | 0 422 631 | 4/1991 | A61M 25/00 |
| WO | WO 00/06230 | 2/2000 | A61M 5/32 |

(Continued)

OTHER PUBLICATIONS

Patricia Jameson, Authorized officer European Patent Office, International Search Report—Application No. PCT/US2014/051217, date of mailing: Nov. 19, 2014 (11 pages), including Written Opinion of the International Searching Authority.

(Continued)

*Primary Examiner* — Rebecca E Eisenberg
(74) *Attorney, Agent, or Firm* — Sunstein Kann Murphy & Timbers LLP

(57) ABSTRACT

A device for stabilizing a patient catheter includes a docking pod with a body, an inlet, an outlet, an internal fluid path between the inlet and the outlet, and a securement surface located on an underside of the docking pod. A docking pod adhesive layer located at least partially on the securement surface of the docking pod may secure the docking pod to the patient such that the securement surface and the docking pod adhesive layer form a generally planar or concave surface when secured to the patient. A valve mechanism located within the internal fluid path of the docking pod may control fluid flow through the docking pod. The device may also have a luer connector that is fluidly connected to the (Continued)

outlet of the docking pod and configured to be connected to the catheter.

29 Claims, 21 Drawing Sheets

Related U.S. Application Data

(60) Provisional application No. 61/866,686, filed on Aug. 16, 2013.

(51) Int. Cl.
| | |
|---|---|
| *A61M 25/02* | (2006.01) |
| *A61M 39/24* | (2006.01) |
| *A61M 39/12* | (2006.01) |
| *A61M 39/22* | (2006.01) |
| *A61M 5/158* | (2006.01) |
| *A61M 39/10* | (2006.01) |

(52) U.S. Cl.
CPC .............. *A61M 5/158* (2013.01); *A61M 39/10* (2013.01); *A61M 2025/0266* (2013.01); *A61M 2025/0273* (2013.01); *A61M 2039/2426* (2013.01)

(58) Field of Classification Search
USPC ...... 604/167.03, 167.04, 174, 179, 180, 247
See application file for complete search history.

(56) References Cited

U.S. PATENT DOCUMENTS

| | | | | |
|---|---|---|---|---|
| 5,865,808 | A | 2/1999 | Corn | 604/174 |
| 6,086,564 | A * | 7/2000 | McLaughlin | A61M 25/02 |
| | | | | 128/DIG. 26 |
| 2010/0298777 | A1* | 11/2010 | Nishtala | A61M 25/02 |
| | | | | 604/174 |
| 2011/0106014 | A1 | 5/2011 | Helm, Jr. | 604/178 |
| 2012/0232490 | A1 | 9/2012 | Andino | 604/180 |
| 2012/0271240 | A1 | 10/2012 | Andino et al. | 604/180 |

FOREIGN PATENT DOCUMENTS

| | | | | |
|---|---|---|---|---|
| WO | WO 02/096494 | 12/2002 | ............ | A61M 25/06 |
| WO | WO 2009/032008 | 3/2009 | ............ | A61M 25/06 |
| WO | WO 2010/132837 | 11/2010 | .............. | A61M 5/32 |

OTHER PUBLICATIONS

International Search Report—Application No. PCT/US2016/042232, mailed on Nov. 8, 2016, together with the Written Opinion of the International Searching Authority, 13 pages.

\* cited by examiner (Shown with attached catheter in side view only)

Step 1  Prime With Saline
- Fill nPatch with standard saline solution until fluid exits cap Step 2 Remove Cap and Return to Tray
• Remove cap on male Luer connector and return nPatch to tray Step 3  Insert Catheter
- Identify optimal vein on hand, clean site and let dry; insert (open) catheter into vein, place gauze under hub, occlude vein and withdraw insertion needle
- Gauze "preserves" docking site Step 4 Attach nPatch to Catheter
- While holding catheter and occluding vein, grasp nPatch by fin and push male Luer into catheter hub until snug
- Discard gauze Step 7 Remove Syringe
• Remove syringe by grasping valve and turning syringe counter-clockwise Step 8 Tighten Luer Connection
- Grasp catheter hub and turn lock collar clockwise until snug Step 9 Flip Film Over
• Unfold nPatch to encompass catheter insertion site while grasping the docking pod Step 10 Remove Dressing Liner "2"
• Remove dressing liner "2" while applying slight pressure upon the docking pod and then gently rub down all sections of the dressing

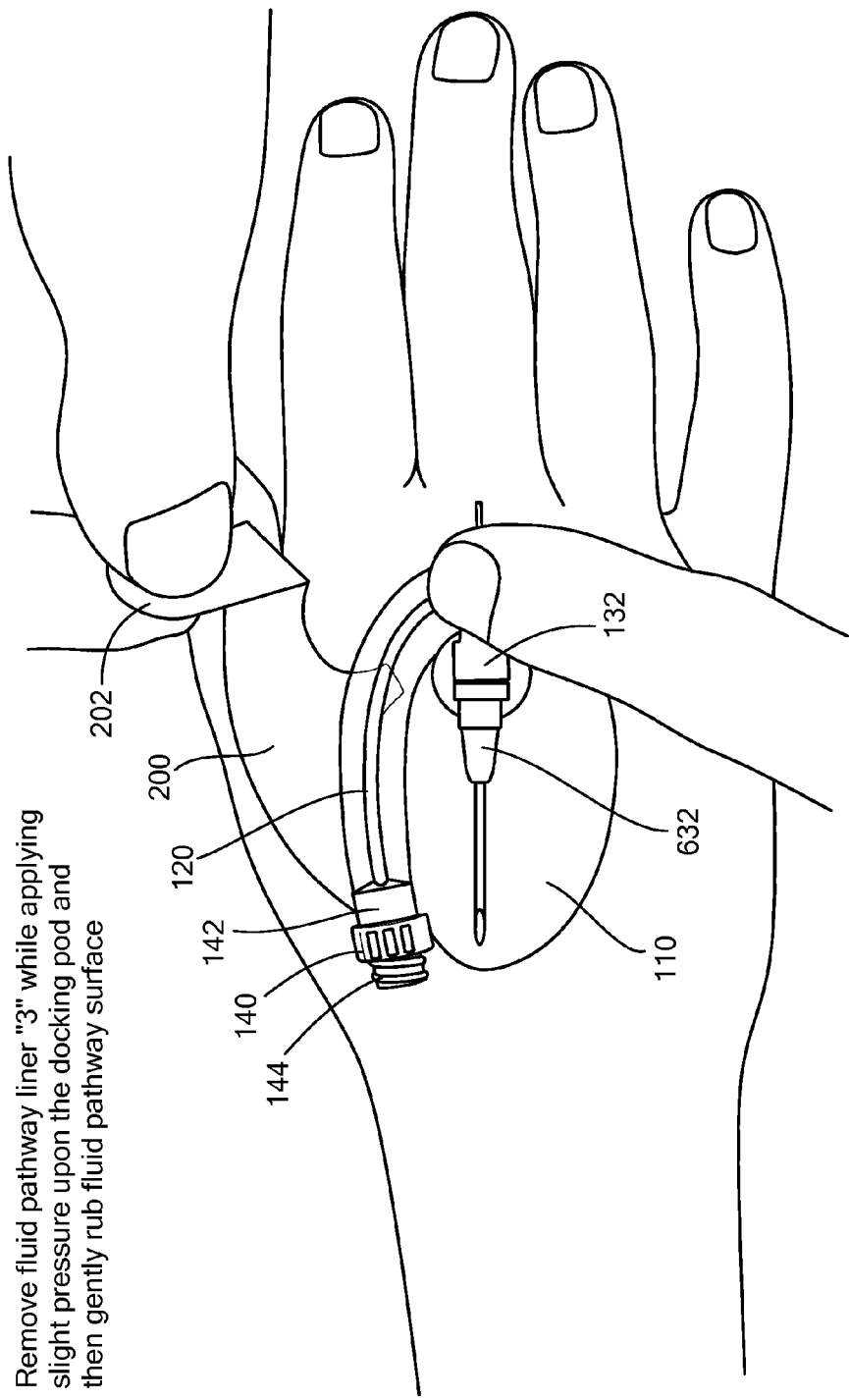

CATHETER CONNECTION AND STABILIZATION DEVICE AND METHODS OF USING SAME

PRIORITY

This patent application is a continuation in part of and claims priority from U.S. patent application Ser. No. 14/408,436, filed Dec. 16, 2014, entitled "Catheter Connection and Stabilization Device and Methods of Using Same," and naming Luis Maseda, Todd Chelak, Nick Dennis, and Ian Kimball as inventors, the disclosure of which is incorporated herein, in its entirety, by reference.

U.S. application Ser. No. 14/408,436, in turn, is a national phase application of and claims priority to PCT Application No. PCT/US2014/051217, filed Aug. 15, 2014, entitled "Catheter Connection and Stabilization Device and Methods of Using Same," and naming Luis Maseda, Todd Chelak, Nick Dennis, and Ian Kimball as inventors, the disclosure of which is incorporated herein, in its entirety, by reference.

PCT Application No. PCT/US2014/051217, in turn, claims priority from U.S. Provisional Patent Application No. 61/866,686, filed Aug. 16, 2013, entitled, "Catheter Connection and Stabilization Device and Methods of Using Same," and naming Luis Maseda, Todd Chelak, Nick Dennis, and Ian Kimball as inventors, the disclosure of which is incorporated herein, in its entirety, by reference.

TECHNICAL FIELD

The present invention relates to devices for securing a catheter to a patient, and more particularly to devices that stabilize and secure catheters to a patient and allow for connection of a medical implement.

BACKGROUND ART

In instances in which a patient will need regular administration of fluid or medications (or regular withdrawal of fluids/blood), catheters are often inserted into the patient and used to administer the fluids/medications. The catheter may remain in the patient for extended periods of time (several hours to several days). Additionally, an extension tube may be connected to the catheter to facilitate use of the catheter and connection of a medical implement (e.g., a syringe). To ensure that the catheter and/or extension tube remain in place and are not accidentally removed, some prior art systems secure the catheter and/or extension tube to the patient using tape or similar adhesive materials (e.g., a film dressing).

Tapes and adhesive film dressings can be problematic in that they may not firmly secure the catheter in place. Additionally, in some instances, the manner in which the tape is applied and the positioning/location of the catheter and/or extension tube may cause the catheter and/or extension tube to be bent. This, in turn, increases the risk of kinking (which can reduce/stop flow through the catheter and/or extension tube) and makes it more difficult to connect the medical implement required to introduce the fluid/medication.

SUMMARY OF THE EMBODIMENTS

In a first embodiment of the invention there is provided a catheter connection and stabilization device that includes a medical valve, a male luer connector for connection to a catheter, and an adherent substrate (e.g., a dressing, tape, or similar substrate having an adhesive). The medical valve may have an open mode that permits fluid flow through the valve and a closed mode that prevents fluid through the valve. The medical valve may also include a housing having an inlet and an outlet. The dressing may have a first and at least a second film layer that at least partially define at least one fluid pathway. The at least one fluid pathway may extend through the dressing between at least two film layers and fluidly connect the outlet of the medical valve and the male luer connector. Alternatively, the fluid path may be formed by the first and second film layers overlaying a third film layer containing a void, the void being encapsulated by the first and second layers. The dressing may also include an adhesive layer located on an underside of the second film layer that is configured to secure the dressing to a patient.

In some embodiments, the medical valve may include a split septum obstructing the inlet of the medical valve, and connection of a medical implement to the inlet of the medical valve may deform the split septum to transition the medical valve from the closed mode to the open mode. The stabilization device may also include a docking pod located between the male luer connector and the at least one fluid pathway. The docking pod, in turn, may include (1) a docking pod adhesive layer located at least partially on the underside of at least a portion of the docking pod for securing the docking pod to the patient, and (2) a pressure activated valve. Alternatively, the docking pod may be mechanically joined to the topside of the dressing with the docking pod adhesive then located on the underside of the dressing for securing the docking pod to the patient. The pressure activated valve may include a diaphragm with a slit through it. The slit may have a cracking pressure above which the slit opens to allow fluid flow through the pressure activated valve. For example, the backward cracking pressure may be greater than the venous pressure of the vein in which the catheter is inserted and may be greater than the forward cracking pressure.

The at least one fluid pathway may have a first fluid volume when the medical implement is connected to the medical valve and a second fluid volume when the medical implement is disconnected from the medical valve. The first fluid volume may be greater than the second fluid volume. Additionally or alternatively, the first film layer and/or the at least second film layer may be formed with a channel that defines at least part of the at least one fluid pathway. The at least one fluid pathway may be resistant to kinking, and the catheter stabilization device may have a neutral fluid displacement at the male luer connector upon disconnection of the medical implement from the medical valve.

The stabilization device may also include an opening extending through the dressing, and a proximal portion of the catheter may extend through the opening when connected to the male luer connector. The dressing may also have a strain relief member that extends from the opening, and allows the dressing to conform to the catheter. The strain relief member may be a notched feature. The dressing may be transparent.

In some embodiments, one or more auxiliary fluid pathways may extend from the at least one fluid pathway through the dressing or adherent substrate. The first and at least second film layers may at least partially define the auxiliary fluid pathway(s). Additionally or alternatively, more than two film layers may define the auxiliary fluid pathways. The auxiliary fluid pathways may extend from the at least one fluid pathway through the dressing between at least two film layers to an internal reservoir and/or an access port. The internal reservoir may provide a means for interacting with a fluid within the fluid pathway, and the access port may be a medical valve. The means for interacting with the fluid within the internal reservoir may include mixing and/or reconstitution of a lyophilized drug contained within the reservoir, analyzing the fluid that comes in contact with an analyzing element contained within and/or forming a wall of the reservoir, and/or other physical, chemical, and biological interactions known in the art of fluid handling.

In accordance with further embodiments, a method for stabilizing a catheter within a patient may include providing a catheter stabilization device. The catheter stabilization device may include a medical valve, a male luer connector and a dressing or an adherent substrate. The medical valve may have an open mode that permits fluid flow through the valve and a closed mode that prevents fluid through the valve. The medical valve may also include a housing having an inlet and an outlet. The dressing may have a first film layer and at least a second film layer that at least partially define at least one fluid pathway extending through the dressing and fluidly connecting the medical valve and male luer connector. The method may also include connecting the catheter to the male luer connector, and adhering at least a portion of the dressing to the patient to secure the catheter stabilization device to the patient and stabilize the catheter.

In some embodiments, the method may also include connecting a medical implement to the inlet of the medical valve, and priming the catheter stabilization device, for example, prior to connection of the catheter to the male luer connector. In such embodiments, the stabilization device may include a vented priming cap located on the male luer connector. The method may remove the priming cap after priming and before connection of the catheter to the male luer connector. Additionally or alternatively, a venting element (e.g., hydrophobic membrane) may form a portion of the catheter stabilization device and may be located within a wall of the at least one fluid pathway between the male luer connector and the valve and therefore, not require removal before connection of the catheter to the male luer connector.

The stabilization device may also include a docking pod (e.g., located between the male luer connector and the at least one fluid pathway) having an internal fluid path and a pressure activated valve mechanism. The docking pod may also have an adhesive at least partially located on at least a portion of an underside of the docking pod, and the method may include securing the docking pod to the patient via the adhesive (e.g., prior to securing the at least a portion of the dressing to the patient). The method may also include checking for flow through the catheter stabilization device and vein by injecting fluid into the vein. If the flow through the catheter stabilization device and vein is inadequate, the method may remove the docking pod from the patient, adjust the location of the catheter within the vein, and re-secure the docking pod to the patient via the adhesive.

In further embodiments, the pressure activated valve mechanism may include a diaphragm with a slit through it. The slit may have a cracking pressure above which the slit opens to allow fluid flow through the pressure activated valve. For example, the backward cracking pressure may be greater than the venous pressure of the vein in which the catheter is inserted and may be greater than the forward cracking pressure. The dressing may include an adhesive layer located on an underside of the second film layer, and adhering the dressing to the patient may include adhering the dressing to the patient via the adhesive layer. At least a portion of the adhesive layer may contain an antimicrobial agent or antiseptic that interacts with the patient's skin after adhering the dressing to the patient.

The medical valve may include a split septum obstructing the inlet of the medical valve, and connection of the medical implement to the inlet of the medical valve may deform the split septum to transition the medical valve from the closed mode to the open mode. Additionally, the at least one fluid pathway may have a first fluid volume when the medical implement is connected to the medical valve and a second fluid volume when the medical implement is disconnected from the medical valve. The first fluid volume may be greater than the second fluid volume. The catheter stabilization device may have neutral fluid displacement at the male luer connector upon disconnection of the medical implement from the medical valve.

The first film layer and/or the second film layer may be formed with a channel that defines at least part of the at least one fluid pathway. The stabilization device may also include an opening extending through the dressing. A proximal portion of the catheter may extend through the opening when connected to the male luer connector. Additionally, a strain relief member extending from the opening may allow the dressing to conform to the catheter. The dressing may be transparent, and the fluid pathway may be resistant to kinking.

In accordance with additional embodiments, a device for stabilizing a patient catheter may include (1) a medical valve having an open mode that permits fluid flow through the valve and a closed mode that prevents fluid flow through the valve, and (2) a male luer connector that connects to the catheter. The medical valve may include a housing having an inlet and an outlet. The device may also include a docking pod, and a docking pod adhesive layer. The docking pod may have an internal fluid path and may fluidly connect to the male luer connector. The docking pod adhesive layer may be at least partially located beneath at least a portion of the docking pod, and may secure the docking pod to the patient. The device may further include an adherent substrate with a first film layer and at least a second film layer. The first and second film layers may at least partially define a fluid pathway that extends through the adherent substrate and fluidly connects the outlet of the medical valve and the docking pod.

In some embodiments, the device may also have an adhesive layer located on an underside of the first film layer. The adhesive layer may secure the adherent substrate or a dressing to the patient. The medical valve may also include a split septum obstructing the inlet of the medical valve, and connection of a medical implement to the inlet may deform the split septum to transition the medical valve from the closed mode to the open mode. Additionally or alternatively, the docking pod may include a pressure activated valve with a diaphragm. The diaphragm may have a slit through it, and the slit may have a cracking pressure above which the slit opens to allow fluid flow through the pressure activated valve. For example, the cracking pressure may be greater than a venous pressure of a vein in which the catheter is inserted.

The fluid pathway may have a first fluid volume when the medical implement is connected to the medical valve and a second fluid volume when the medical implement is disconnected from the medical valve. The first fluid volume may be greater than the second fluid volume. The first film layer and/or the second film layer may be formed with a channel that defines at least part of the fluid pathway.

In further embodiments, the device may include an opening that extends through the dressing, and the catheter may extend through the opening when connected to the male luer connector. Additionally or alternatively, the device may also have a strain relief member extending from the opening. The strain relief member may allow the dressing to conform to the catheter. The dressing may be transparent and the fluid pathway may be resistant to kinking. The device may also have neutral fluid displacement upon disconnection of a medical implement from the medical valve, and may include a venting element located within a wall of the fluid pathway. The venting element may allow priming of the fluid pathway.

In some embodiments, the device may include a third layer located between the first and second layers. The third layer may have a channel that at least partially defines the fluid pathway. Additionally, the second film layer may include a first hole and a second hole extending through the second film layer. The first hole may be configured to create fluid communication between an inlet of the docking pod and the fluid pathway. The second hole may be configured to create fluid communication between the outlet of the medical valve and the fluid pathway.

In accordance with still further embodiments, a method for stabilizing a patient catheter may include providing a catheter stabilization device having a medical valve, a male luer connector, a docking pod, a docking pod adhesive layer, and an adherent substrate. The medical valve may have an open mode that permits fluid flow through the valve and a closed mode that prevents fluid through the valve, and may include a housing with an inlet and an outlet. The male luer connector may connect to a catheter. The docking pod may have an internal fluid path, and may fluidly connect to the male luer connector. The docking pod adhesive layer may be at least partially located beneath at least a portion of the docking pod, and may secure the docking pod to the patient. The adherent substrate may have a first film layer and a second film layer that at least partially define a fluid pathway that extends through the adherent substrate and fluidly connects the medical valve and docking pod.

The method may also include connecting the catheter to the male luer connector, and adhering at least a portion of the adherent substrate to the patient to secure the catheter stabilization device to the patient and stabilize the catheter. The adherent substrate may also include a third layer located between the first and second layers. The third layer may have a channel that at least partially defines the fluid pathway. Additionally, the second film layer may include a first hole and a second hole extending through the second film layer. The first hole may be configured to create fluid communication between an inlet of the docking pod and the fluid pathway, and the second hole may be configured to create fluid communication between the outlet of the medical valve and the fluid pathway.

In accordance with further embodiments, a device for stabilizing a patient catheter includes a docking pod having a body, an inlet, an outlet, an internal fluid path between the inlet and the outlet, and a securement surface located on an underside of the docking pod. The device also includes (1) a docking pod adhesive layer located at least partially on the securement surface of the docking pod, (2) a valve mechanism, and (3) a luer connector. The docking pod adhesive layer may be configured to secure the docking pod to the patient. The securement surface and the docking pod adhesive layer may form a generally planar or concave surface when secured to the patient. The valve mechanism may be located within the internal fluid path of the docking pod, and may be configured to control fluid flow through the docking pod. The luer connector (e.g., a male luer connector) may be fluidly connected to the outlet of the docking pod and configured to be connected to the catheter.

The valve mechanism may be a pressure activated valve. For example, the pressure activated valve may include a diaphragm having a slit therethrough. The slit may have a cracking pressure above which the slit opens to allow fluid flow through the pressure activated valve. The proximally-directed cracking pressure (i.e. pressure exerted from the catheter side) may be greater than a venous pressure of a vein in which the catheter is inserted. The distally-directed cracking pressure may be different than the proximally-directed cracking pressure.

In some embodiments, the securement surface stabilizes the device on the patient. The device may also include a fin extending from the body of the docking pod. The fin may be releasably secured to the body of the docking pod via a hinge that is configured to allow the fin to be moved relative to the body. Alternatively, the fin may be integral to and non-movable relative to the body. The docking pod adhesive layer and/or securement surface may be configured to deform to the patient to create the generally planar or concave surface.

In accordance with additional embodiments, a method for stabilizing a patient catheter includes providing a catheter stabilization device having a docking pod with body, an inlet, an outlet, an internal fluid path between the inlet and the outlet, and a securement surface located on an underside of the docking pod. The device may also have (1) a docking pod adhesive layer located at least partially on the securement surface of the docking pod, (2) a valve mechanism located within the internal fluid path of the docking pod and configured to control fluid flow through the docking pod, and (3) a luer connector fluidly connected to the outlet of the docking pod and configured to be connected to the catheter. The docking pod adhesive layer may be configured to secure the docking pod to the patient. The method may also include connecting the catheter to the luer connector, and adhering at least a portion of the securement surface of the docking pod to the patient via the adhesive layer to secure the docking pod to the patient and stabilize the catheter. The securement surface and the docking pod adhesive layer may form a generally planar surface or concave surface when secured to the patient.

The valve mechanism may be a pressure activated valve, and may include a diaphragm having a slit therethrough. The slit may have a cracking pressure above which the slit opens to allow fluid flow through the pressure activated valve. The proximally-directed cracking pressure may be greater than a venous pressure of a vein in which the catheter is inserted. The distally-directed cracking pressure may be different than the proximally-directed cracking pressure. The securement surface may stabilize the device on the patient. Additionally or alternatively, the device may have a fin extending from the body of the docking pod. The fin may be releasably secured to the body of the docking pod via a hinge that allows the fin to be moved relative to the body. Alternatively, the fin may be integral to and non-movable relative to the body. In some embodiments, adhering the securement surface to the patient causes the docking pod adhesive layer and/or securement surface to deform to the patient to achieve the general contour of the patient's body at the securement site.

In accordance with still further embodiments, a device for stabilizing a patient catheter includes a docking means, a securement means for securing the docking means to the patient, a valve means for controlling fluid flow through the docking means, and a connection means for connecting the catheter to the docking means. The docking means may have a body, an inlet, an outlet, an internal fluid path between the inlet and the outlet, and a securement surface located on an underside of the docking means. The securement means may be located at least partially on the securement surface of the docking means. The securement surface and the securement means may form a generally planar or concave surface when secured to the patient. The valve means may be located within the internal fluid path, and the connection means may be fluidly connected to the outlet of the docking means.

The valve means may be pressure activated, and may include a diaphragm having a slit therethrough. The slit may have a cracking pressure above which the slit opens to allow fluid flow through the pressure activated valve. The proximally-directed cracking pressure may be greater than a venous pressure of a vein in which the catheter is inserted. The distally-directed cracking pressure may be different than the proximally-directed cracking pressure. The securement surface may stabilize the device on the patient. Additionally or alternatively, the device may include a grasping means extending from the body of the docking means. The grasping means may be secured to the body of the docking means via a hinge that allows the grasping means to be moved relative to the body. Alternatively, the grasping means may be integral to and non-movable relative to the body. The securement means may be configured to deform to the patient to create the generally planar or concave surface.

In accordance with additional embodiments, a device for stabilizing a patient catheter includes a docking pod having a body, an inlet, an outlet, an internal fluid path between the inlet and the outlet, and a securement surface located on an underside of the docking pod. The device may also include (1) a docking pod adhesive layer located at least partially on the securement surface of the docking pod, (2) a pressure activated valve mechanism located within the internal fluid path of the docking pod and configured to control fluid flow through the docking pod, (3) a luer connector fluidly connected to the outlet of the docking pod and configured to be connected to the catheter, and (4) a fin extending off a surface of the docking pod. The docking pod adhesive layer may be configured to secure the docking pod to the patient. The luer connector may be fluidly connected to the outlet of the docking pod and configured to be connected to the catheter. The fin may be configured to provide a surface for grasping and manipulating the docking pod.

The pressure activated valve may include a diaphragm having a slit therethrough. The slit may have a cracking pressure above which the slit opens to allow fluid flow through the pressure activated valve. The proximally-directed cracking pressure may be greater than a venous pressure of a vein in which the catheter is inserted. The fin may be releasably secured to the body of the docking pod via a hinge that allows the fin to be moved relative to the body. The hinge may be a living hinge, and/or the fin may be ribbed or knurled. Alternatively, the fin may be integral to and non-movable relative to the body.

BRIEF DESCRIPTION OF THE DRAWINGS

The foregoing features of embodiments will be more readily understood by reference to the following detailed description, taken with reference to the accompanying drawings, in which:

FIGS. 10A-10L show the catheter connection and stabilization device shown in FIG. 1 being secured to a patient and stabilizing a catheter, in accordance with illustrative embodiments of the present invention.

DETAILED DESCRIPTION OF SPECIFIC EMBODIMENTS

In illustrative embodiments, a catheter connection and stabilization device may be secured to a patient to hold a catheter inserted into a patient's body in place. Some embodiments may include a medical valve and a male luer connector that are fluidly connected to one another via a fluid pathway extending through an adherent substrate (e.g., a dressing, tape, or similar substrate having an adhesive). In this manner, various embodiments may provide for the connection of a medical implement (e.g., a syringe) and the transfer of fluids in/out of the patient through the catheter and stabilization device. Details of illustrative embodiments are discussed below.

Figure 1:
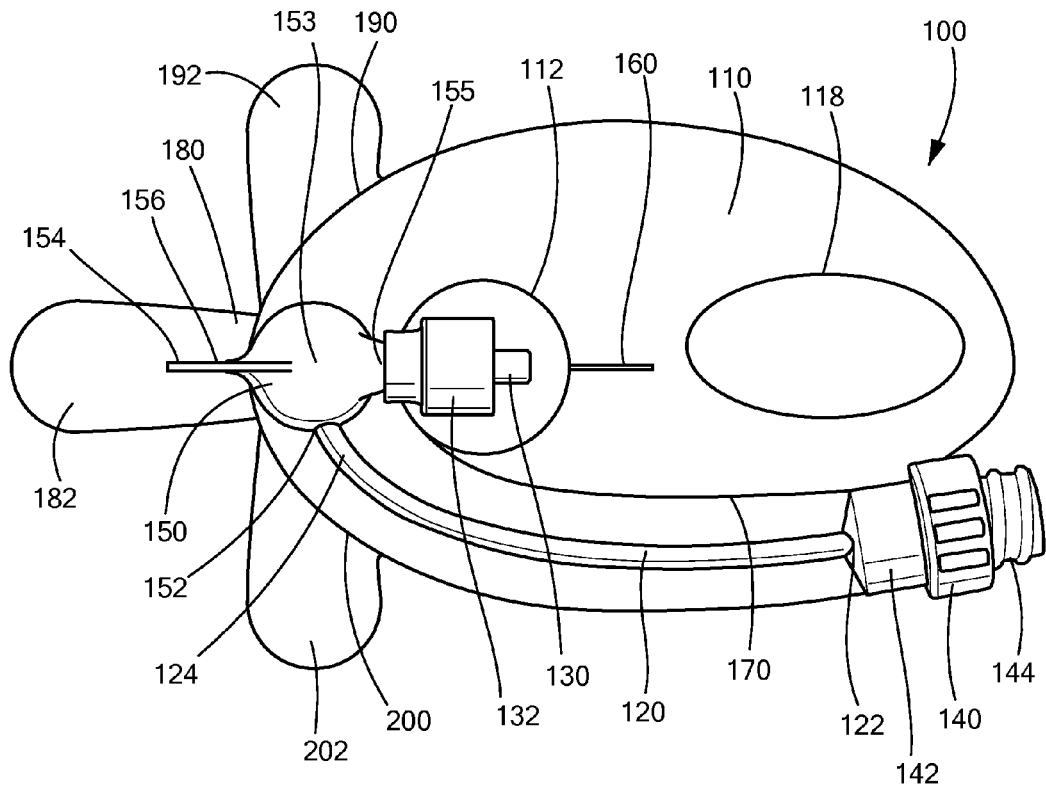
FIG. 1 schematically shows a catheter connection and stabilization device, in accordance with various embodiments of the present invention.

FIG. 1 schematically shows a catheter connection and stabilization device 100 in accordance with some embodiments of the present invention. The stabilization device 100 may include a dressing portion 110 (e.g., a transparent dressing or an adherent substrate) that may be applied to the patient, and a fluid pathway 120. More specifically, the dressing portion 110 may include an adhesive layer on its underside to secure the stabilization device 100 to the patient. Although any number of adhesives may be used to secure the stabilization device 100 to the patient, the adhesive should be strong enough such that the dressing portion 110 and the stabilization device 100 do not peel off the patient's skin during regular movement by the patient (e.g., manipulation of the hand, arm etc.).

In some embodiments, the part of the dressing portion 110 containing the fluid pathway 120 also includes a medical valve 140 (discussed in greater detail below) to control fluid flow through the stabilization device 100. This part of the dressing 110 also has a skin contacting adhesive (e.g., a tacky silicone adhesive) that allows that part of the dressing portion 110 to be removed from the skin (e.g., to allow access to the medical valve 140) and re-adhered to the skin after the medical valve 140 has been accessed.

Figure 2:
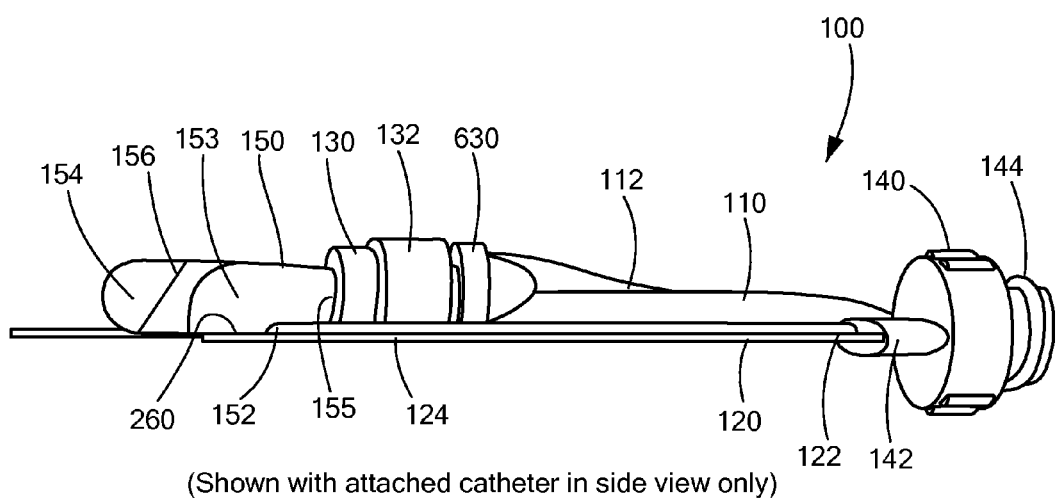
FIG. 2 schematically shows a side view of the catheter connection and stabilization device shown in FIG. 1, in accordance with some embodiments of the present invention.
Figure 4A:
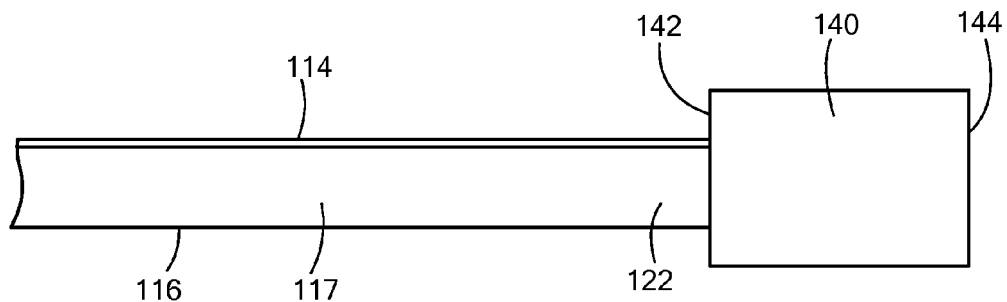
FIG. 4A schematically shows a first embodiment of a fluid pathway formed within the catheter connection and stabilization device, in accordance with some embodiments of the present invention.
Figure 4B:
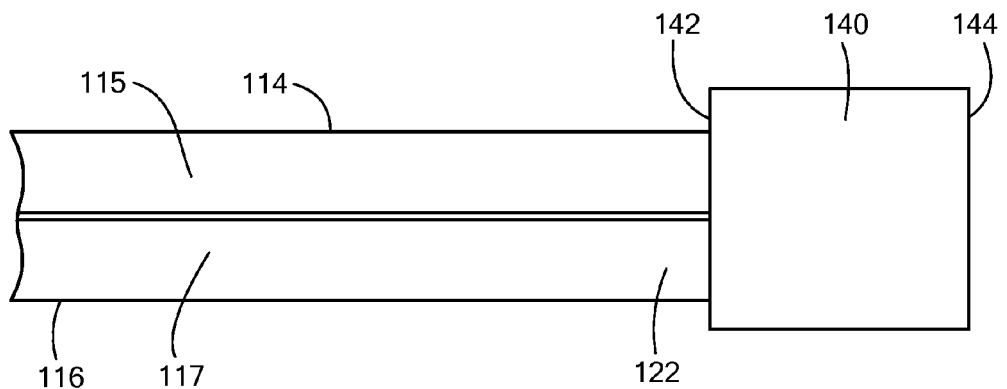
FIG. 4B schematically shows an alternative embodiment of a fluid pathway formed within the catheter connection and stabilization device, in accordance with some embodiments of the present invention.

The dressing portion 110 may also have an opening 112, through its body. This opening 112 allows a proximal portion of a catheter 630 (FIG. 2) to pass through the stabilization device 100. Additionally, as discussed in greater detail below, the dressing portion 110 can be made from multiple layers of film (e.g., a first layer 114 and a second layer 116, FIGS. 4A/B) that define a fluid pathway 120 extending through the dressing portion 110. The layers of film (and thus the dressing portion 110) should be flexible so that the dressing portion 110 can conform to the contours of the patient's skin and allow for manipulation by the user when attaching the stabilization device 100 to the catheter 630. The layers of film can be made from any number of materials including, but not limited to polyurethane, polyester, polyethylene, and/or PVC. To prevent inadvertent stoppage of fluid flow through the stabilization device 100 and catheter 630, the fluid pathway 120, in some embodiments, may be resistant to kinking. It is important to note that, although FIGS. 4A and 4B show only two layers of film, as discussed in greater detail below, other embodiments can have more than two layers and the fluid pathways may extend through the various layers of film.

The dressing portion 110 may be transparent so that the user is able to see and monitor the catheter insertion site, as well as view the fluid flow through the fluid pathway 120. Additionally or alternatively, the dressing portion 110 may include a transparent window 118 on/through part of the dressing portion 110 for viewing/monitoring the insertion site. Although the size of this window 118 can depend on the type of catheter used (e.g., a long hub or a short hub catheter) and the specific application, in preferred embodiments, the window 118 should be at least 1" in diameter and/or length to provide a sufficient viewing area. Additionally, the window 118 may include an adhesive layer on at least a portion of the underside of the window 110. The adhesive layer may contain an antimicrobial agent and/or antiseptic (e.g., Chlorhexidine Gluconate) that interacts with the patient's skin at the catheter insertion site.

As mentioned above, some embodiments enable a medical implement to transfer fluids through a catheter 630 (FIG. 2) inserted into a patient. To that end, the stabilization device 100 includes a male luer connector 130 that is connectable to the catheter 630, and a medical valve 140 (noted above) that is connectable to the medical implement and used to control fluid flow to and from the patient. As shown in FIG. 1, the fluid path 120 may extend between the valve 140 and the male luer connector 130 to allow fluid flow into/out of the patient through the stabilization device 100. For example, the first end 122 of the fluid path 120 may be fluidly connected to the outlet 142 of the valve 140 and the other end 124 of the fluid path 120 may be fluidly connected to the inlet of the male luer connector 130 (or a docking pod 150 which, in turn, is fluidly connected to the male luer connector 130, discussed in greater detail below).

Although any number of medical valves 140 can be used (e.g., positive displacement valves, negative displacement valves, neutral displacement valves, etc.), some embodiments may use a simple split septum valve 140. As is known in the art, a split septum valve includes a septum obstructing the inlet 144 of the valve 140. To allow flow through the valve 140, the septum may include an aperture or a slit extending through it. To that end, connection of the medical implement (e.g., a needleless syringe) to the valve 140 deforms the septum, thus opening the aperture/slit. Once connected, the medical implement may transfer fluid to/from the patient. Additionally or alternatively, some embodiments may include a female luer connector (not shown) located between the fluid pathway 120 and the valve 140 to allow the medical valve 140 to be removed and/or replaced.

As mentioned above and as shown in FIGS. 1-3, some embodiments may also include a docking pod 150 between the second end 124 of the fluid path 120 and the male luer connector 130. The docking pod 150 essentially acts as the hub of the stabilization device 100, through which fluid being transferred to/from the patient flows and to which the other components of the stabilization device 100 (e.g., the fluid pathway 120, the dressing 110, the catheter 630, and/or the valve 140) may be secured/connected. Additionally, as discussed in greater detail below, the docking pod 150 also provides a rigid structure to hold onto when positioning (or repositioning) the stabilization device 100, and helps to keep the dressing 110 out of the way when securing the stabilization device 100 to the patient. Furthermore, because the docking pod 150 may itself be secured to the patient (via adhesive), the docking pod 150 also helps stabilize the catheter 630.

Figure 3:
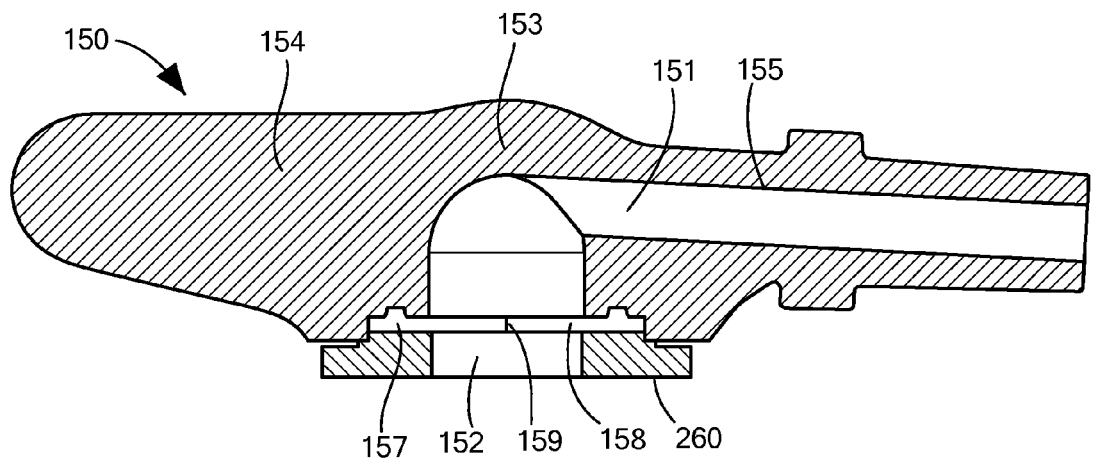
FIG. 3 schematically shows a cross-sectional view of the docking pod shown in FIGS. 1 and 2, in accordance with some embodiments of the present invention.

As best shown in FIG. 3, the docking pod 150 may have a main body 153 with first port 152 (e.g., an inlet) connectable to the fluid path 120, a second port 155 (e.g., outlet), a securement surface 260 that may be used to secure the body 153 to the patient, and an internal fluid path 151 extending through the body 153 of the docking pod 150. As discussed in greater detail below, during use, fluid may flow through the docking pod 150 (e.g., into the inlet 152, through the fluid path 151, and out the outlet 155) as fluid is transferred to the patient. It should be noted that, although much of the discussion herein refers to the first port 152 as an inlet, and the second port 155 as an outlet, the first and second ports 152 and 155 also may be respectively used as outlet and inlet ports. In other words, if fluid is to be drawn from the patient (as opposed to transferred to the patient), the fluid may flow into the second port/outlet 155, through the internal fluid path 151, and out of the first port/inlet 152.

To control fluid flow through the stabilization device 100 and the docking pod 150, the interior of the docking pod 150 itself may include a valve mechanism 157 within the internal fluid path 151. For example, the docking pod 150 may include a two-way pressure activated valve 157 (PAV) that includes a flat diaphragm 158 with a slit 159. Alternatively, at least a portion of the diaphragm 158 may have a curvature with the slit 159 positioned within the curved portion. The valve mechanism 157 prevents fluid flow through the docking pod 150 (e.g., through the internal fluid path 151) until it is exposed to a large enough pressure to open the slit through the diaphragm (e.g., a cracking pressure). It is important to note that a diaphragm 158 and slit 159 configuration should be chosen such that the patient's venous pressure is below the backward (i.e. proximally-directed) cracking pressure of the valve mechanism 157 to prevent the venous pressure from opening the slit 159/pressure activated valve 157. Additionally, the distally-directed cracking pressure may be different than the proximally-directed cracking pressure.

Although a diaphragm 158 with a slit 159 may achieve the functionality of a two-way pressure activated valve, other two-way PAVs known in the art may also be used within the docking pod 150. Additionally or alternatively, the docking pod 150 may include a one-way PAV valve that only allows a one directional flow through the docking pod 150 (e.g., from the inlet to the outlet or from the outlet to the inlet). For example, in some embodiments, the diaphragm 158 may not have a slit 159 (e.g., it may be a solid diaphragm). In such embodiments, the diaphragm may deform (e.g., it may deform over a protrusion within the docking pod 150) in the presence of a pressure within the docking pod 150 to open the internal fluid path 151 and allow the fluid to flow past the diaphragm and through the docking pod 150.

Like the dressing portion 110, the docking pod 150 may also include adhesive on the underside (e.g., on the securement surface 260) to allow the docking pod 150 to be secured to the patient. It should be noted that the shape of the securement surface 260 and/or the adhesive layer impacts the stability of the device 100 when secured to the patient, and convex shaped surfaces may create instability when the device 100 is secured (e.g., the convex surface may cause the device 100 to rock when on the patient). To that end, the securement surface 260, alone or in conjunction with the adhesive layer, should have a generally planar or concave surface. In this manner, the generally planar or concave surface contacting the patient (e.g., the securement surface 260 and adhesive layer) will stabilize the device 100 on the patient. Alternatively or in addition, the securement surface 260 and/or the adhesive layer may be deformable to achieve the general contour of the patient's body at the securement site and to stabilize the docking pod 150.

It is important to note that the term "generally planar" or "planar" as used herein refers to a surface that has a net planar surface when measured/viewed between the ends of the surface (e.g., from end to end). Such planar surfaces may or may not be flat. For example, the generally planar surface may have various features (e.g., ribs, grooves, indents, recesses, bumps, etc.) located between the ends of the surface, as long as the overall profile of the surface from end to end is generally planar.

To create the generally planar surface (or the concave surface) discussed above, both the securement surface 260 and the adhesive layer may be planar. Alternatively, the securement surface 260 may be non-planar, and the adhesive layer may be applied such that the overall profile of the combination of the securement surface 260 and the adhesive layer is generally planar. For example, if the securement surface 260 is convex in shape, the adhesive layer can be applied such that it is thicker at the ends of the securement surface 260 than in the middle, thus creating the planar (or flat) overall profile. Similarly, if the securement surface 260 has a large indent or recess, the portion of the adhesive layer applied to the area of the indent/recess may be thicker than the portion applied to the non-recessed area to create the overall planar (or flat) profile.

In other embodiments, the adhesive layer may simply have the same profile as the securement surface 260 (e.g., convex, indented, etc.) when the device 100 is not secured to the patient. In such embodiments, as the device 100 is secured to the patient, the adhesive layer and/or securement surface 260 may deform/mold to the patient to achieve the general contour of the patient's body at the securement site. For example, if the device is secured to a planar surface on the patient, the adhesive layer and/or securement surface 260 will deform to create a substantially planar surface. Alternatively, if the device 100 is secured to a convex portion on the patient (e.g., on the side of the wrist), the adhesive layer and/or securement surface 260 will deform to create a concave profile/surface.

Alternatively, the docking pod may be mechanically joined to the topside of the dressing with the docking pod adhesive then located on the underside of the dressing for securing the docking pod to the patient (e.g., the docking pod adhesive may be located at least partially beneath the docking pod 150). Additionally, as discussed in greater detail below, the docking pod 150 may also include a grasping element (e.g., grasping fin 154) that extends from the body 153 of the docking pod 150. In such embodiments, the grasping fin 154 may be used to hold the stabilization device 100 and help the user secure the stabilization device 100 to the patient. For example, as the name suggests, the grasping fin 154 may be a relatively long thin structure with flat/planar surfaces on either side. The flat/planar surfaces may be sized to allow an average user to grasp (e.g., using their thumb and forefinger) the fin 154 and, therefore, the device 100. To allow the grasping fin 154 to be moved/adjusted (e.g., during or after securing the stabilization device 100 to the patient), in some embodiments the grasping fin 154 may include a hinge 156 (e.g., a living hinge) that allows the fin 154 to flex/move with respect to the rest of the docking pod 150. Alternatively, the fin 154 may be removable from the docking pod 150.

The grasping fin 154 may be a separate structure that extends from the body 153 of the docking pod 150, or a portion of the body 153 may be shaped to form the fin 154. Although the grasping element is described above as a fin 154, it should be noted that other grasping structures may be used. For example, the grasping element may be a protrusion, a projection, or a vane extending from the body 153 of the docking pod 150. Additionally, in some embodiments, the grasping element may be ribbed, knurled, or have other features (e.g., indents) that help improve the user's ability to grab and/or grasp the grasping element.

The stabilization device 100, and particularly the dressing portion 110, can also include a number of other features that make the stabilization device 100 easier to connect to and stabilize the catheter 630, and secure to the patient. For example, the dressing portion 110 can include a strain relief member 160 (e.g., a cut partially extending through the dressing portion 110, a perforated area, a C-shaped notch, a V-shaped notch, etc.) extending from the opening 112 in the dressing portion 110. The strain relief member 160 allows the dressing portion 110 to conform to the shape of the catheter 630 without wrinkling/folding or tenting (e.g., creation of an air gap between the dressing portion 110 and the skin of the patient) of the dressing portion 110. Additionally, the dressing portion 110 can include a perforated slit extending from the opening 112 and along the portion of the dressing 110 that defines the fluid path 120. Like the strain relief member 160, the perforated slit 170 allows the dressing portion 110 and the stabilization device 100 to better conform to the contours of the patient (e.g., the patient's arm). Additionally, if the perforated slit 170 is at least partially separated, the slit 170 may allow for separation of the valve 140 from the dressing portion 110 to facilitate connection to the valve 140 and reduce incidental forces applied to the dressing portion 110 adjacent to the transparent window 118.

A number of the components of the stabilization device 100 may include one or more adhesive formulations to secure the stabilization device 100 to the patient. To prevent the adhesive from inadvertently sticking to the wrong surface and/or to prevent bacteria and other contamination from sticking to the adhesive, the stabilization device 100 may include one or more liners covering the adhesive. Each of the liners may include a tab so that the liner can be easily removed (discussed in greater detail below). For example, the stabilization device 100 can include a docking pod liner 180 and docking pod liner tab 182 for the adhesive located beneath the docking pod 150 (e.g., on the bottom of the docking pod 150 itself or on the underside of the portion of the dressing on which the docking pod 150 sits), a dressing liner 190 and dressing liner tab 192 for the adhesive located on the underside of the dressing 110, and a fluid pathway liner 200 and fluid pathway liner tab 202 for the adhesive area under the fluid pathway 120. Alternatively, a single liner may be removed to expose multiple adhesive locations and/or formulations.

As mentioned above, the at least two film layers 114/116 of the dressing portion 110 can define the at least one fluid pathway 120 extending between the medical valve 140 and the male luer connector 130 (or docking pod 150). To that end, the fluid pathway 120 may be an area in which the first and second layers 114/116 are not adhered to one another and/or one or more of the layers can be formed with a channel that defines the fluid pathway 120. For example, as shown in FIG. 4A, the second layer 116 (or the first layer 114) can be formed such that it defines a channel 117 through which the fluid may flow. In such embodiments, the first layer 114 (or the second layer 116 if the first layer 114 is formed with the channel) may cover the channel 117 to complete the fluid pathway 120. Alternatively, as shown in FIG. 4B, both the first layer 114 and the second layer 116 may be formed with a channel (e.g., the first layer 114 may be formed with a first channel 115 and the second layer 116 may be formed with a second channel 117) that define the fluid pathway 120. To avoid/minimize device failure, the fluid pathway 120 should be able to withstand high pressures (e.g., at least 325 PSI). Additionally, to allow the stabilization device 100 and the fluid pathway 120 to be primed (discussed in greater detail below), the pathway 120 may include a venting element (not shown) within a wall of the fluid pathway that allows air to pass until the priming fluid contacts (and opens) the valve mechanism 157 in the docking pod 150. In this manner, some embodiments of the fluid pathway 120 may be self-priming.

Figure 5:
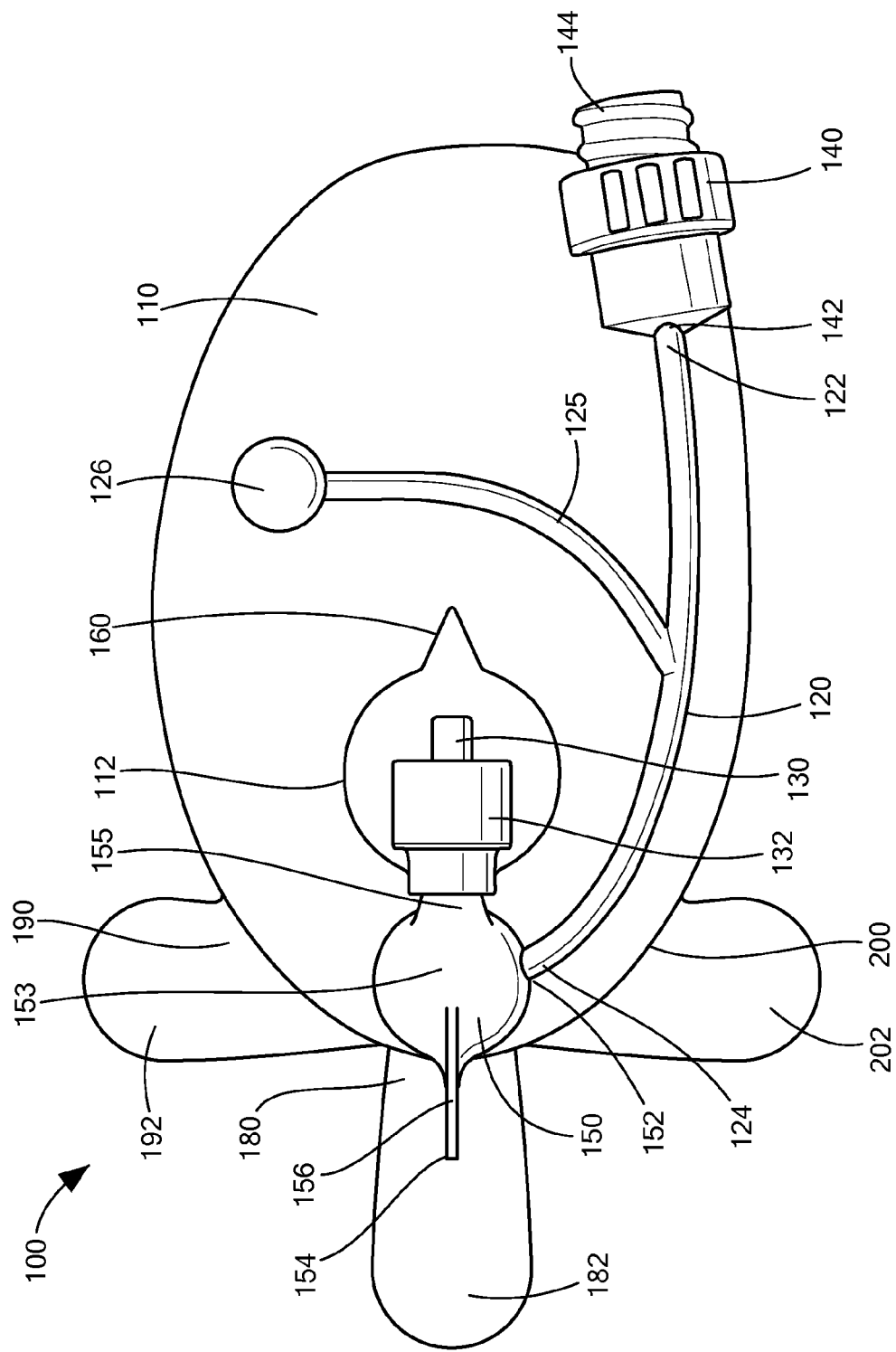
FIG. 5 schematically shows an alternative embodiment of a catheter connection and stabilization device having multiple fluid pathways, in accordance with additional embodiments of the present invention.

As mentioned above, some embodiments of the present invention can have more than one fluid pathway extending between the layers of the dressing portion 110. For example, as shown in FIG. 5, some embodiments may include an additional fluid pathway 125 (or multiple additional fluid pathways) fluidly connected to and extending from the first fluid pathway 120. This additional fluid pathway 125 may lead to a reservoir 126 (or an access port, medical valve, etc.) that, in turn, may contain a liquid to be administered to the patient via the additional fluid pathway. Additionally or alternatively, the reservoir 126 may contain a drug (e.g., a lyophilized drug) that is to be mixed with the fluid entering the reservoir 126 and subsequently administered to the patient. The reservoir 126 and/or the additional fluid pathway can also include an analyzing element that analyzes the fluid that comes into contact with the element. For example, the analyzing element may be contained within and/or form a wall of the reservoir 126 or the additional fluid pathway 125.

Figure 6A:
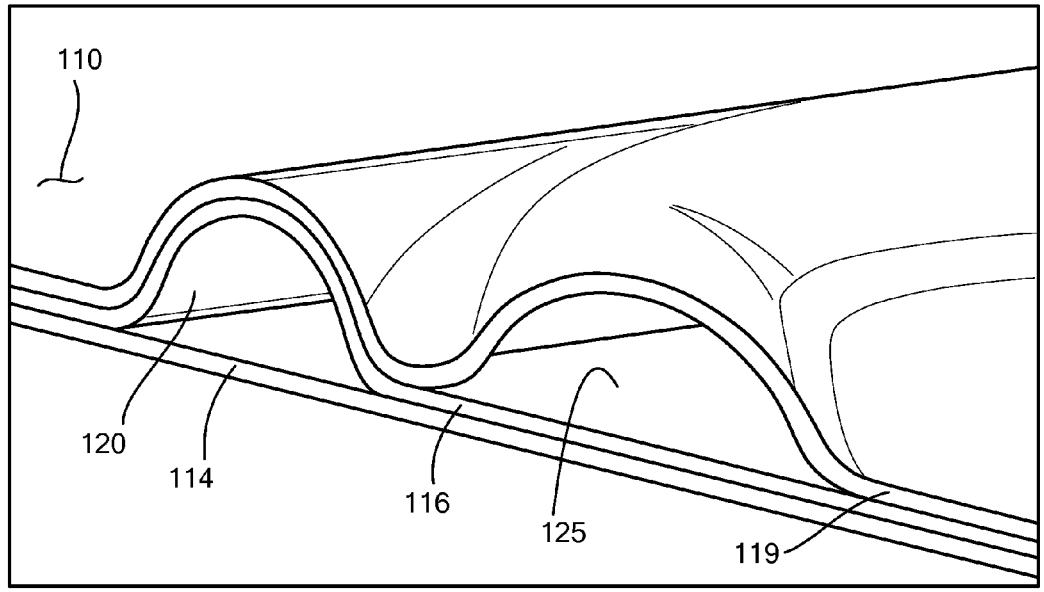
FIG. 6A schematically shows a first multiple fluid pathway configuration formed within the catheter connection and stabilization device, in accordance with some embodiments of the present invention.
Figure 6B:
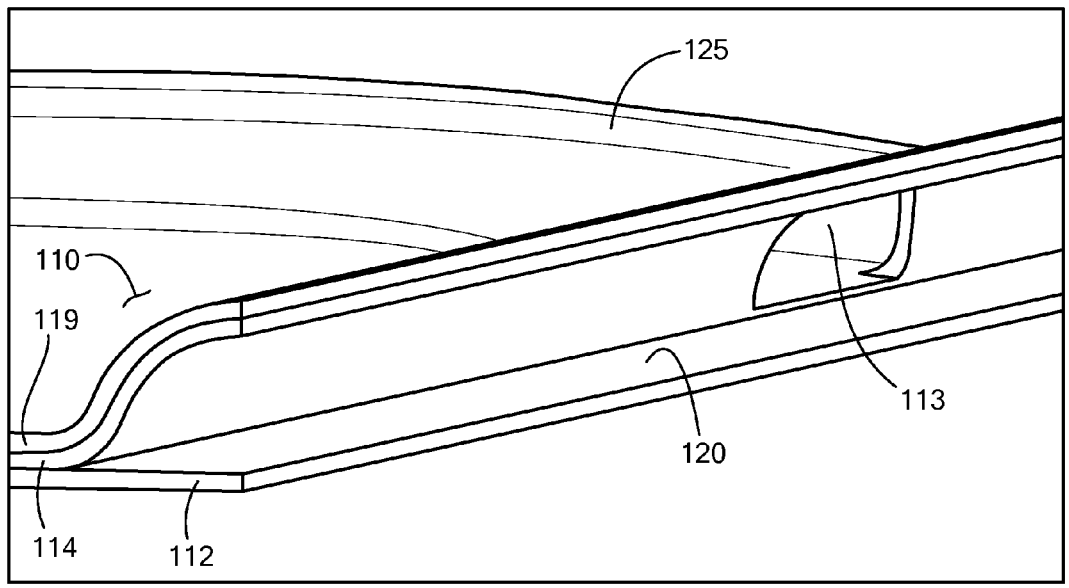
FIG. 6B schematically shows an alternative view of the multiple fluid pathway configuration shown in FIG. 6A, in accordance with some embodiments of the present invention.
Figure 6C:
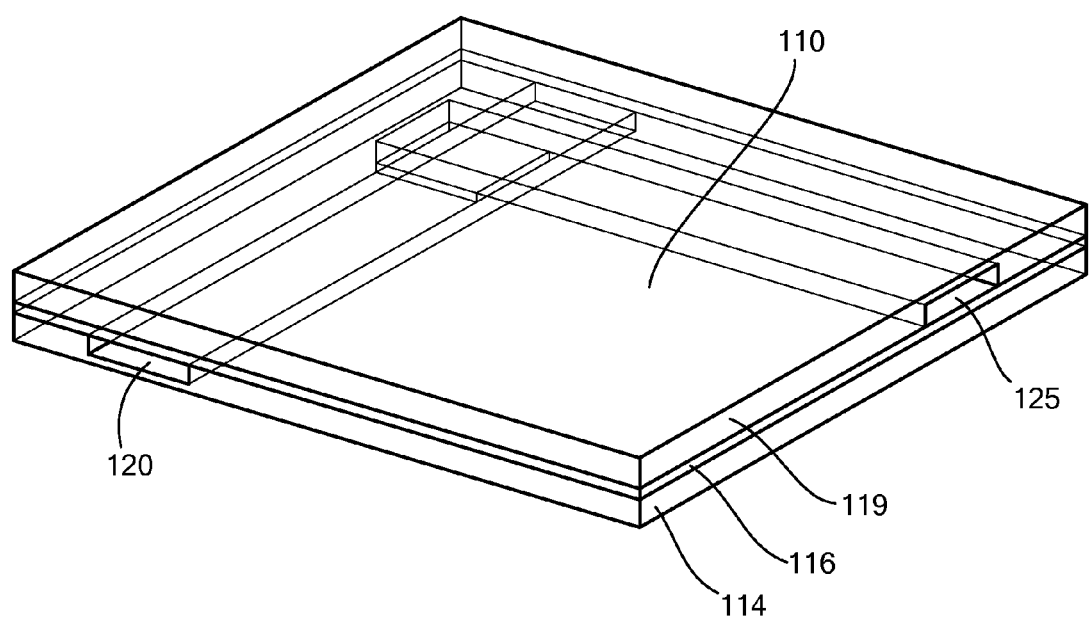
FIG. 6C schematically shows a further alternative multiple fluid pathway configuration formed within the catheter connection and stabilization device, in accordance with some embodiments of the present invention.

It is important to note that the additional fluid pathway 125 may extend through the same two layers of film as the first fluid pathway 120 (e.g., layers 114 and 116) or the additional fluid pathway 120 may extend between different layers of film. For example, as shown in FIGS. 6A through 6C, the additional fluid pathway 125 may extend between the second layer of film 116 and a third layer of film 119. To facilitate fluid flow between the fluid pathways 120/125 and between the film layers, as best shown in FIG. 6B, the second film layer 114 can include an opening 113 that fluidly connects the first fluid pathway 120 and the additional fluid pathway 125 through the second film layer 114. In some embodiments, the additional fluid pathway 125 can be a one-way fluid path that allows fluid to flow from the first fluid pathway 120 to the second fluid pathway 125 and/or reservoir 126, but not back to the first fluid pathway 120.

Although FIGS. 6A-6C show embodiments having three layers 114/116/119 and two fluid paths (e.g., fluid pathway 120 and additional fluid pathway 125), other embodiments can have more than three layers and more than two pathways. For example, some embodiments may include 4 or more layers of film and three or more fluid pathways. The fluid pathways may extend between (and be formed by) the same layers of film or they may extend between different layers of film (e.g., there may only be a single fluid pathway between any two layers, multiple fluid pathways between any two layers, or a single fluid pathway between some layers and multiple pathways between others).

Figure 7:
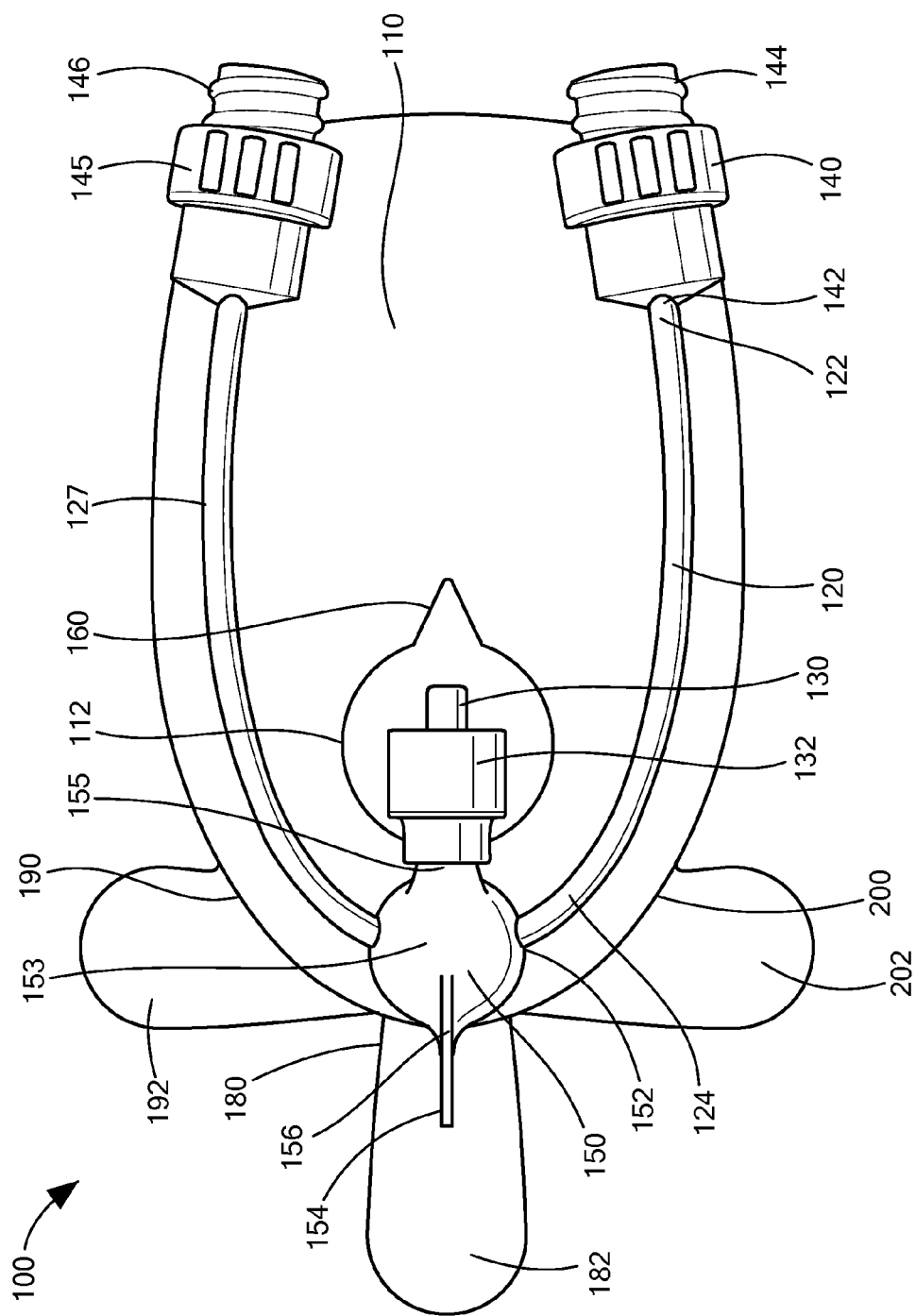
FIG. 7 schematically shows an alternative embodiment of a catheter connection and stabilization device having multiple fluid pathways and medical valves, in accordance with additional embodiments of the present invention.

As shown in FIG. 7, in some embodiments, the catheter stabilization device 100 may have multiple medical valves. In such embodiments, in addition to the medical valve 140 shown in FIG. 1, the stabilization device 100 may include a second medical valve 145 to which a medical implement may be connected (e.g., to the inlet 146 of the medical valve 145). Like the first medical valve 140, the second medical valve 145 may be fluidly connected to the docking pod 150 via a fluid pathway 127 extending between the two or more film layers 114/116/119 forming the dressing portion 110 (e.g., between the first and second film layers 114/116, between the second and third film layers 116/119, etc.). Like the first medical valve 140, the second medical valve 145 can be used to transfer fluid between the patient (e.g., into or out of the patient) and a medical implement.

Figure 8A:
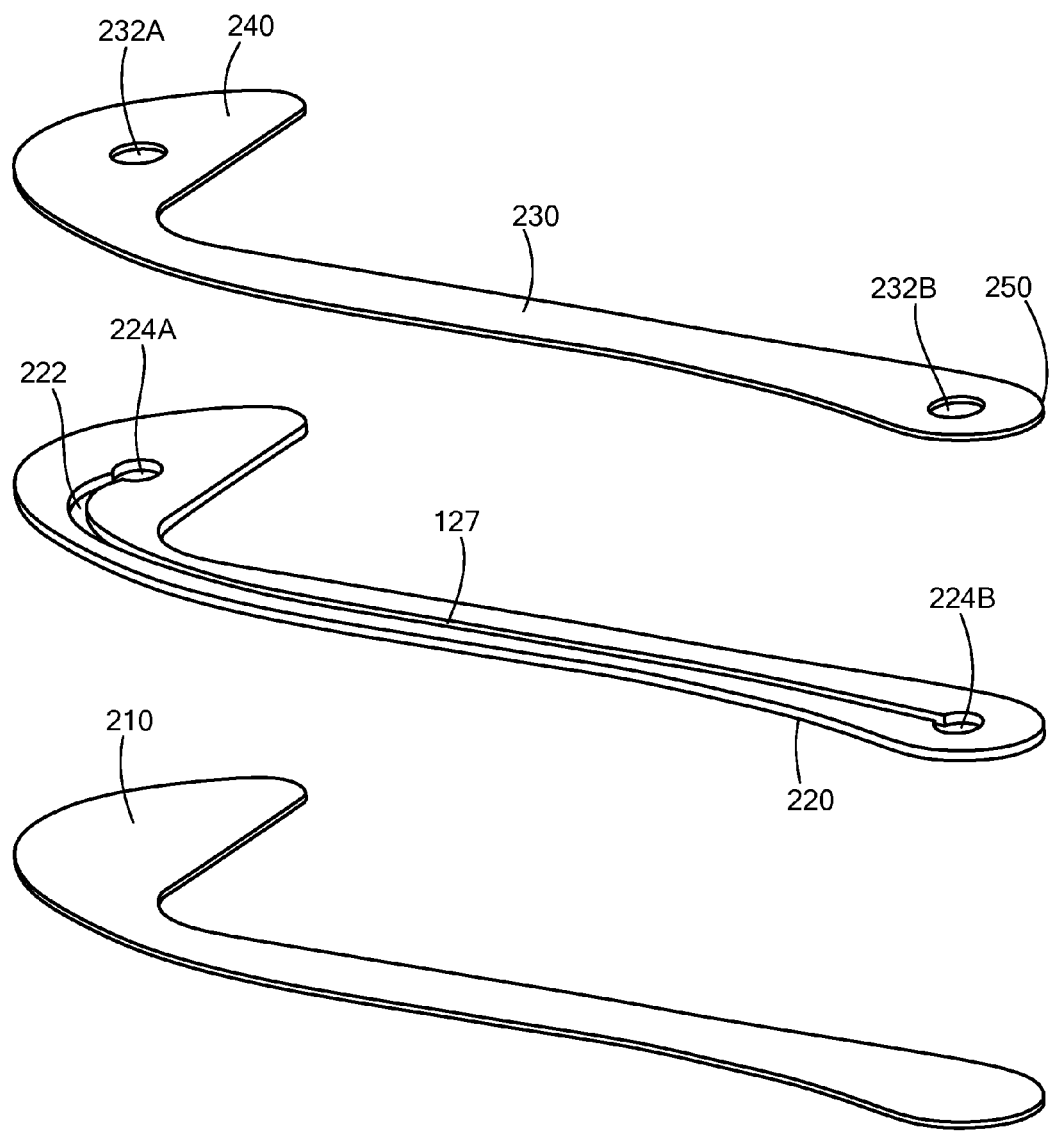
FIG. 8A schematically shows an exploded view of an alternative embodiment of an adherent substrate portion of catheter connection and stabilization device, in accordance with some embodiments of the present invention.
Figure 8B:
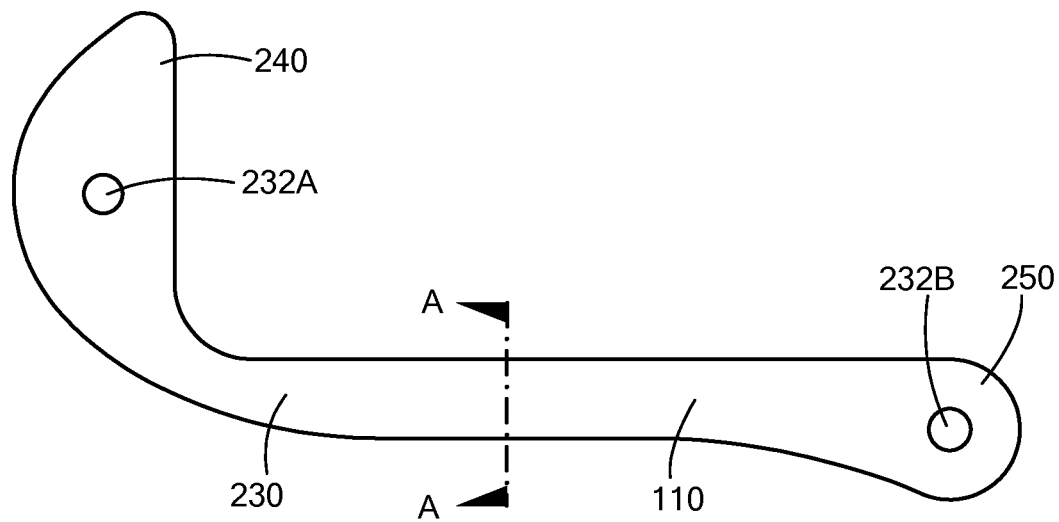
FIG. 8B schematically shows an assembled top view of the adherent substrate portion shown in FIG. 8A, in accordance with some embodiments of the present invention.
Figure 8C:
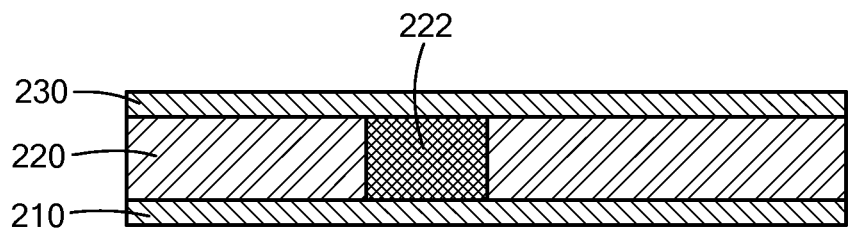
FIG. 8C schematically shows a cross sectional view of the adherent substrate portion shown in FIGS. 8A and 8B along line A-A, in accordance with embodiments of the present invention.

As noted above, some embodiments of the catheter stabilization device 100 can have more than two layers of film, and the fluid pathway(s) can extend within/through the various layers. For example, as shown in FIGS. 8A-8C, the catheter stabilization device 100 can have three layers of film that make up the dressing portion 110 (or just the portion containing the fluid path 120 extending between the valve 140 and the docking pod 150, and the portion on which the docking pod 150 resides). The dressing portion 110 (or just the portion containing the flow path 120) may have a first/bottom layer 210 on which the various adhesive areas discussed above may be located (e.g., on the underside of the first/bottom layer 210), and a second/top layer 230. The first layer 210 and the second layer 230 may be essentially flat and envelope a third/middle layer 220 between them.

As best shown in FIG. 8A, the third/middle layer 220 includes a channel 222 formed within it. This channel 222 may form the fluid pathway 127, and may extend between two enlarged areas 224A/224B at either end of the channel 222. To facilitate the flow of fluid through the second/top layer 230 and facilitate fluid communication with the docking pod 150 and valve 140, the second/top layer may include through holes 232A/232B that are aligned with the enlarged areas 224A/224B within the channel 222, FIGS. 8A and 8B. For example, the docking pod 150 may be located at one end 240 of the second/top layer 230, and the second/top layer 230 may have a first hole 232A that is aligned with enlarged area 224A to facilitate fluid communication between the channel 222 and the inlet 152 of the docking pod 150. Similarly, the medical valve 140 may be located on/secured to the opposing end 250 of the dressing portion 110, and the second/top layer 230 may have a second hole 232B that is aligned with enlarged area 224B to facilitate fluid communication between the channel 222 and the outlet 142 of the medical valve 140. To that end, when transferring a fluid to the patient, fluid may pass through the medical valve 140 and second hole 232B, and into the channel 222. The fluid may then flow through the channel 222, out of the first hole 232A, and enter the inlet 152 of the docking pod 150.

Although FIGS. 8A-8C only show the portion of the dressing 110 on which the docking pod 150 is located and through which the fluid pathway 127 extends, it is important to note that the three layer configuration may extend to the rest of the dressing portion 110 (e.g., the dressing portion shown in FIG. 1). Alternatively, in some embodiments, only the first/bottom layer 210 and/or the second/top layer 230 may extend further to form the remainder of the dressing portion 110 (e.g., the third/middle layer may only be located in the portion shown in FIGS. 8A to 8C and may not extend to the rest of the dressing portion 110).

It is important to note that, depending on the valve mechanism used within the docking pod 150 (if equipped) and/or the type of medical valve 140 used, the stabilization device 100 and the fluid pathway 120 may be exposed to changing pressures during disconnection and connection of the medical implement. For example, if the medical valve 140 is a split septum valve, connection of the medical implement to the valve 140 may increase the pressure within the fluid pathway 120 (e.g., because the medical implement will take up volume within the medical valve 140 and the pressure activated valve in the docking pod 150 is closed). Furthermore, once fluid transfer is complete and the pressure activated valve closes, removal of the medical implement from the valve 140 will create a negative pressure/vacuum within the fluid pathway 120.

To compensate for this change in pressure, in some embodiments, the fluid pathway 120 may be compliant such that it has a first volume when the medical implement is connected to the valve 140 and a second volume when the medical implement is disconnected. For example, as the medical implement is connected to the valve 140 and the pressure within the fluid pathway 120 increases, the fluid pathway 120 may expand to compensate for the increase in pressure. Conversely, as the medical implement is disconnected from the medical valve 140 and the pressure decreases, the fluid pathway 120 may decrease in volume (but not fully collapse) to compensate for the decrease in pressure. In this manner, various embodiments of the present invention are able to ensure that the pressure differential between the downstream and upstream side of the pressure activated valve is not above the cracking pressure. Furthermore, by compensating for the change in pressure and volume created by connection/disconnection of the medical implement, some embodiments can attain neutral fluid displacement performance at the male luer connector 130 upon connection and/or disconnection of the medical implement to the valve 140.

Figure 9:
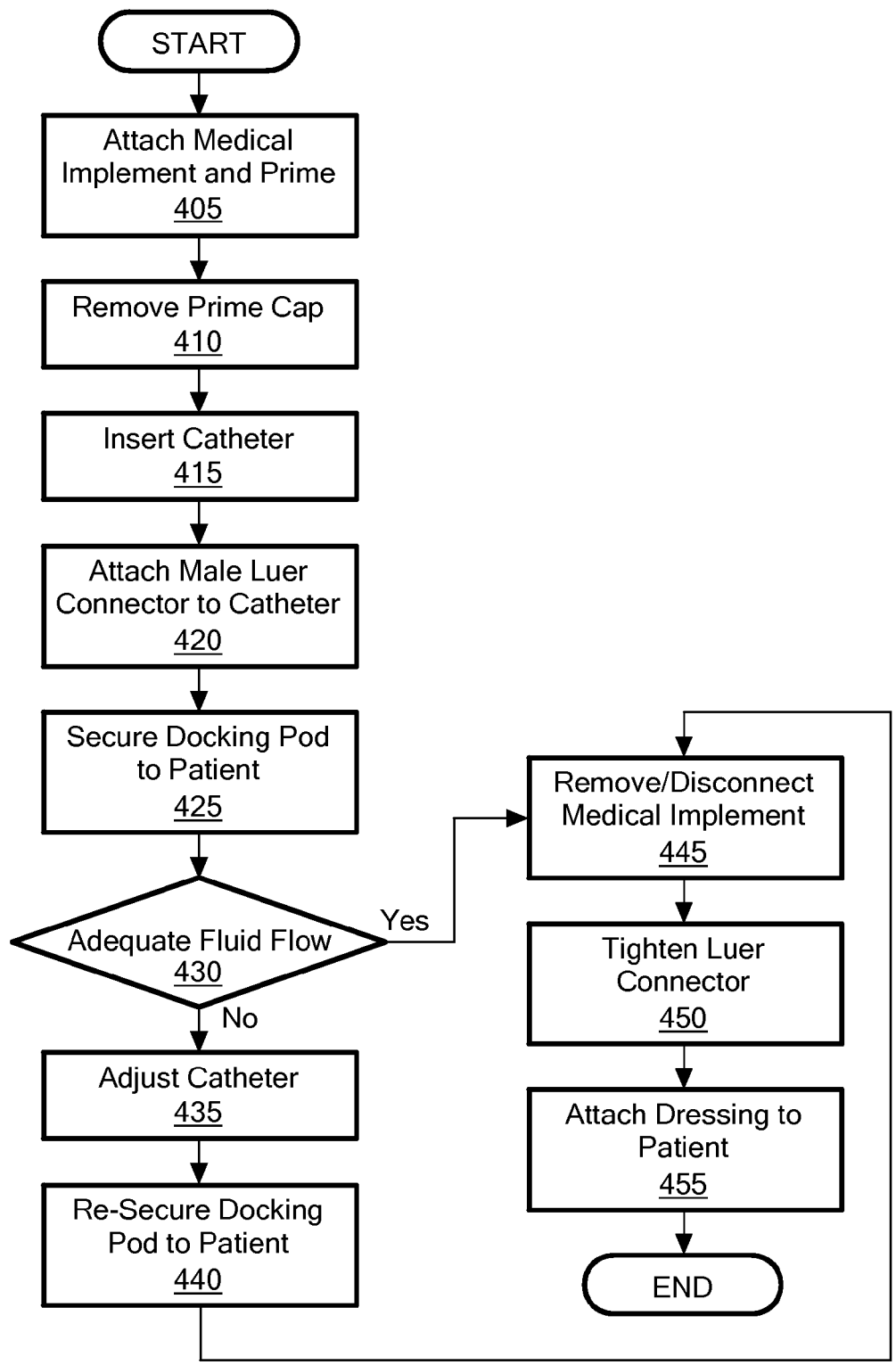
FIG. 9 is a flowchart showing a method of securing a catheter connection and stabilization device to a patient to stabilize a catheter, in accordance with illustrative embodiments of the present invention.
Figure 10A:
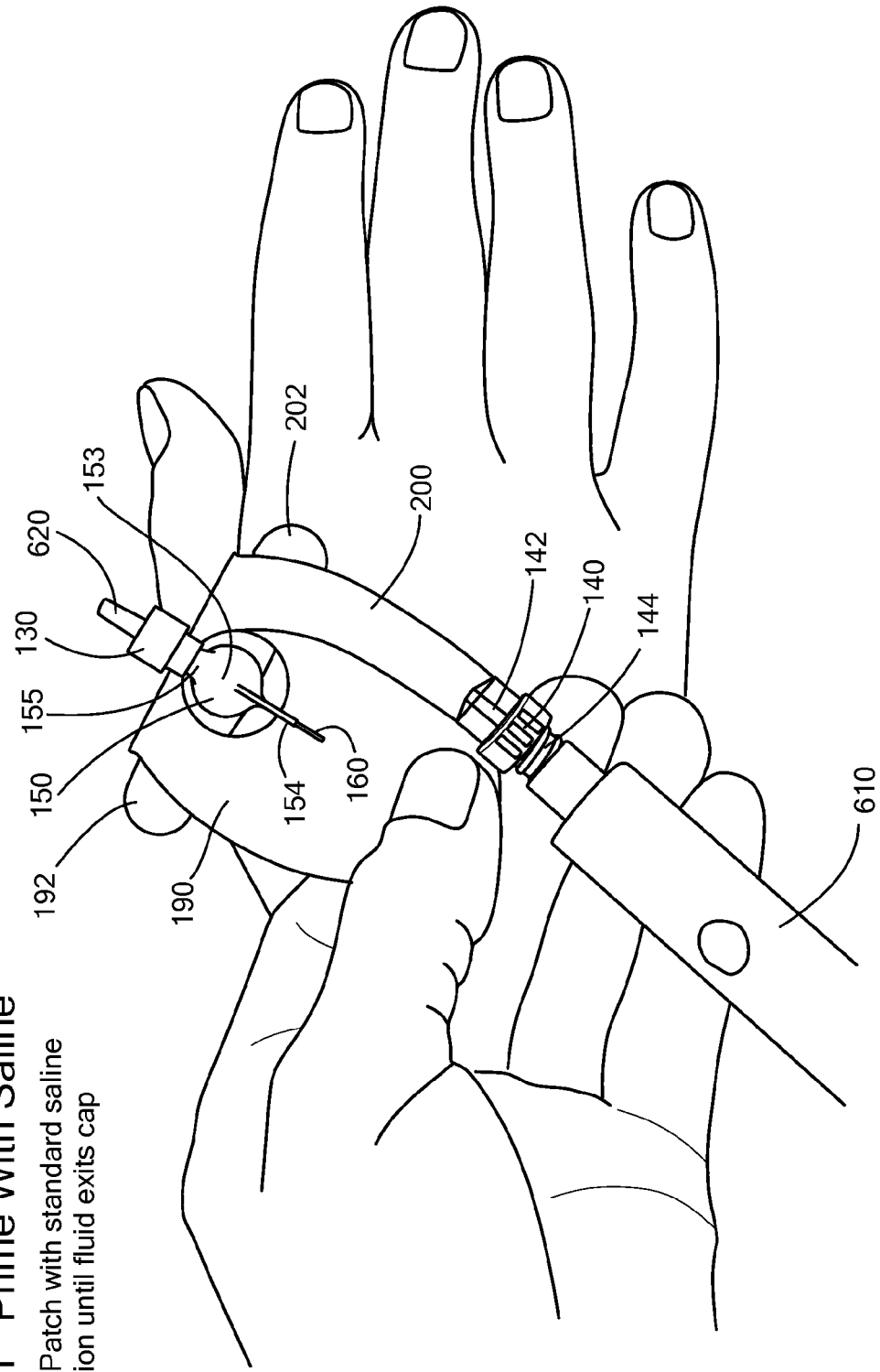
Figure 10B:
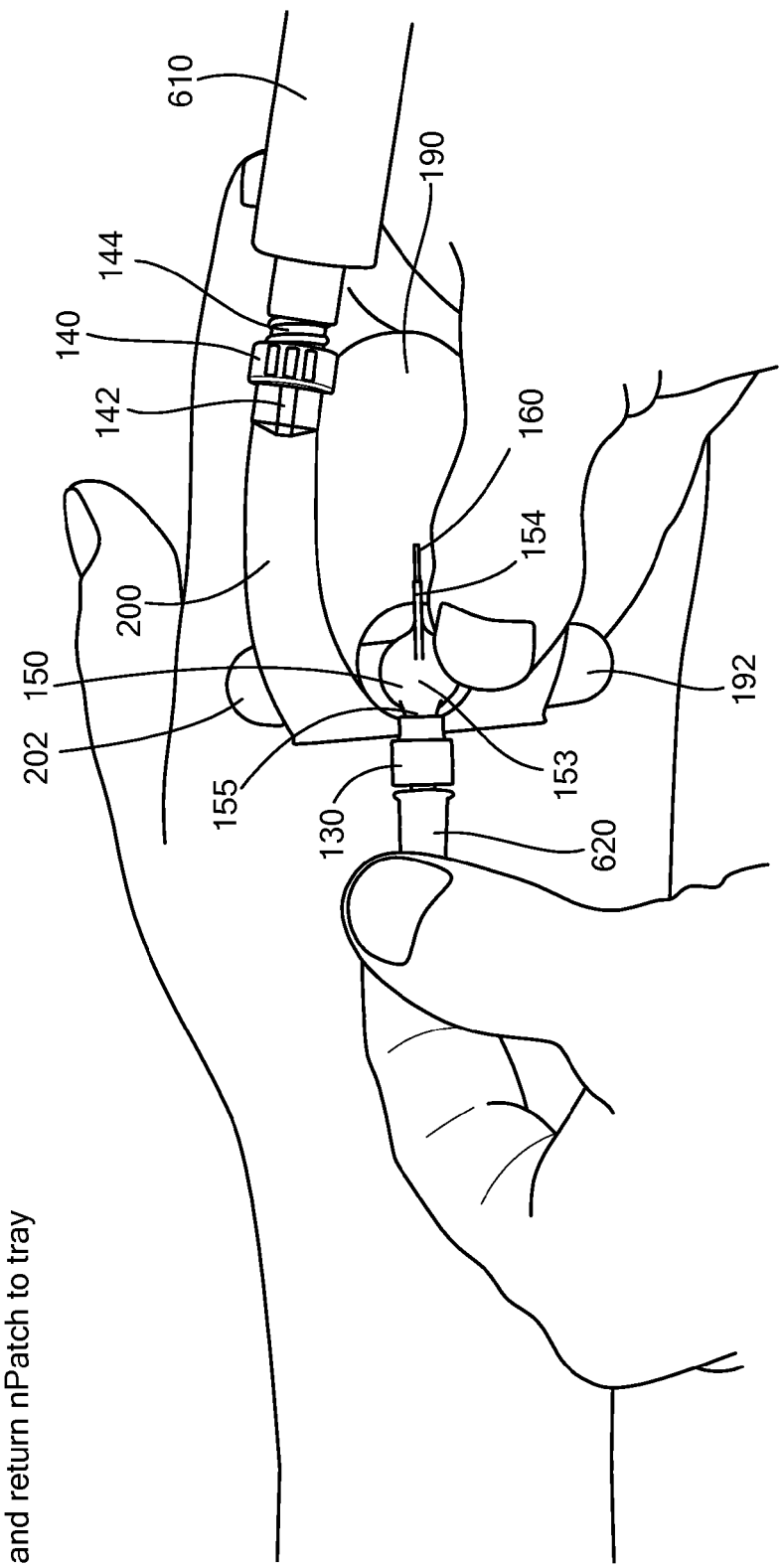

FIG. 9 is a flowchart depicting a method for stabilizing a catheter 630 using a stabilization device 100 in accordance with various embodiments of the present invention. FIGS. 10A-10L schematically show the catheter connection and stabilization device 100 at various stages of securement and stabilizing of the catheter 630. First, the user (e.g., the medical personnel) may connect a medical implement 610 to the valve 140 and flush (e.g., prime) the stabilization device 100, for example, with saline (Step 405, FIG. 10A). As shown in FIG. 10A, the stabilization device 100 may include a priming cap 620 located on/secured to the male luer connector 130. The priming cap 620 may be a vented cap that allows air (and priming fluid) to escape (e.g., as saline is introduced into the stabilization device 100), but helps prevent particulates from entering the male luer connector 130. If the stabilization device 100 has a second medical valve 145, a similar priming procedure may be performed on the second medical valve 145. Additionally, it is important to note that, if the fluid pathway 120 or the additional fluid pathway 145 includes a venting element, air will exit the fluid pathway(s) 140/145 via the venting element during the priming process to prime the fluid pathways 140/145.

Figure 10C:
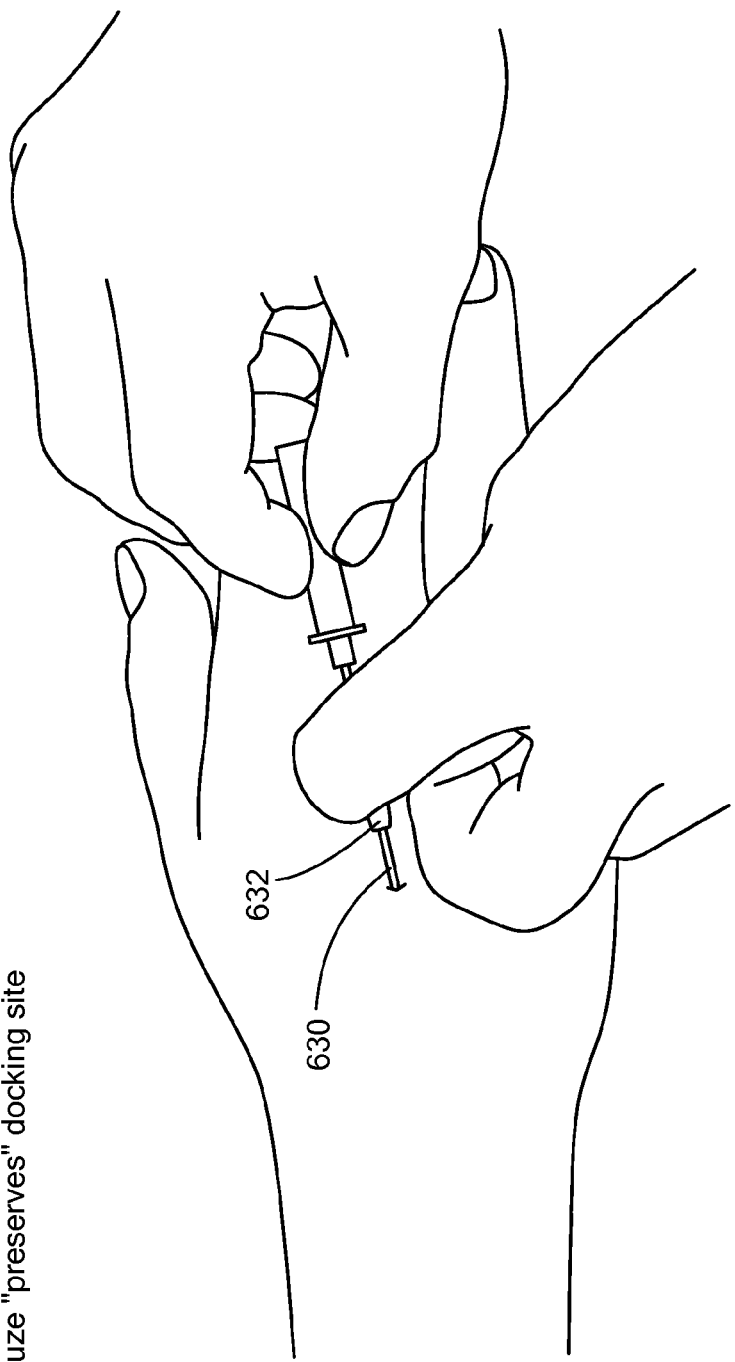
Figure 10D:
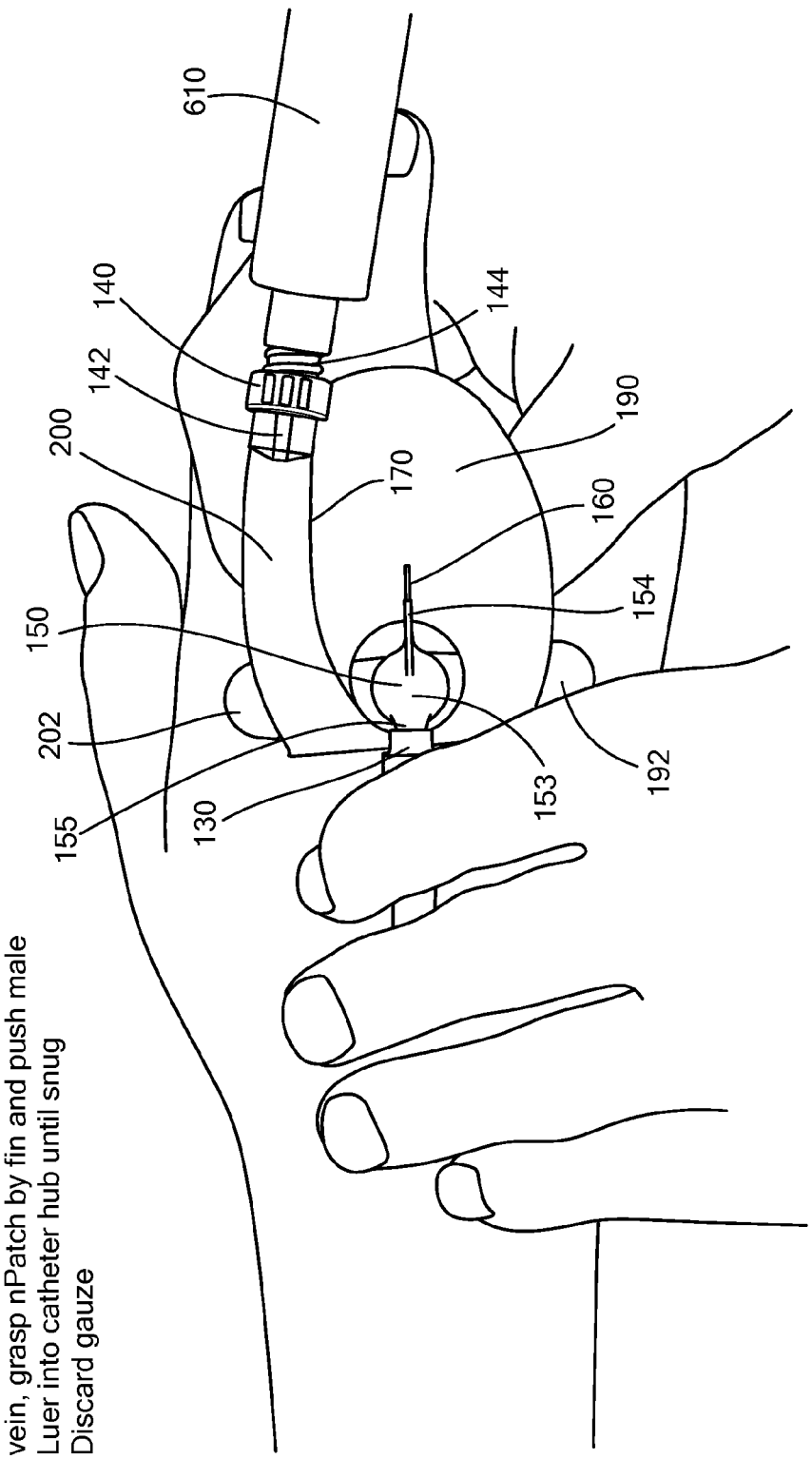
Figure 10E:
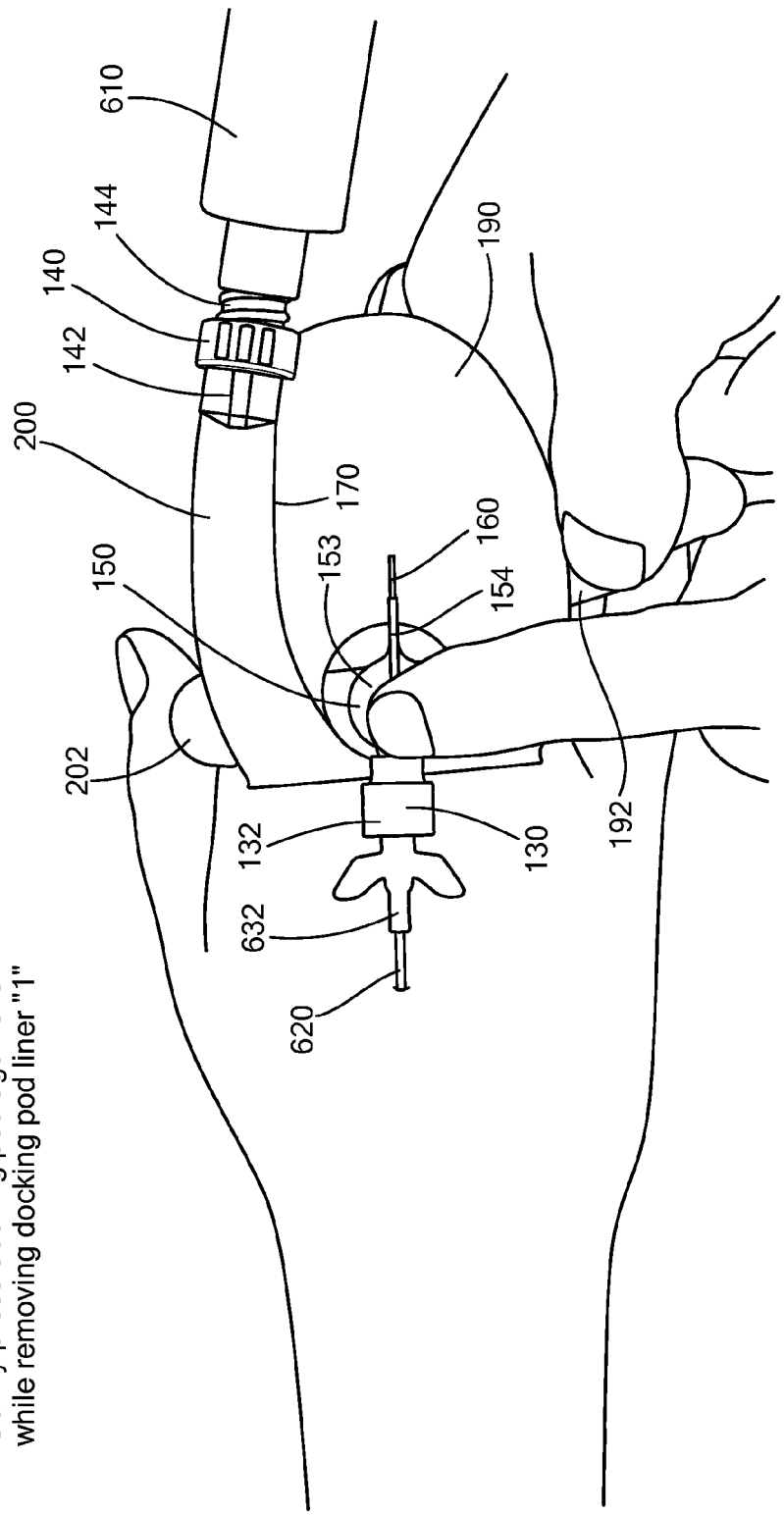

Once the stabilization device is flushed/primed, the user may remove the priming cap 620 (Step 410, FIG. 10B) and insert the catheter 630 into the patient (e.g., into the patient's arm) (Step 415, FIG. 10C). It is important to note that prior to inserting the catheter 630, the insertion site should be properly cleaned per acceptable medical practice. Additionally, to preserve the injection site after insertion of the catheter 630, the user may place gauze over the injection site and the location where the stabilization device 100 will be placed. The user may then connect the male luer connector 130 to the catheter 630 (Step 420; FIG. 10D).

As shown in FIG. 10D-10H, when attaching the catheter 630 and securing the stabilization device 100, it may be helpful to fold a portion of the stabilization device 100 over (or the stabilization device 100 can be packaged in the folded configuration). For example, the dressing portion 110 can be folded over such that the opening 112 is located over the docking pod 150 and the grasping fin 154 extends through the opening 112 and contacts the underside of the dressing portion 110. In this manner, the grasping fin 154 acts to keep the dressing portion 110 out of the way of the user during connection of the catheter 630. Once the catheter 630 is attached to the male luer connector 130, the user may then remove the docking pod liner 180 (e.g., by pulling on the docking pod liner tab 182) to expose at least a portion of the adhesive beneath the docking pod, and press the docking pod 150 against the skin of the patient to secure the docking pod 150 to the patient (Step 425, FIG. 10E). It is important to note that the adhesive beneath the docking pod may not be a single adhesive formulation. For instance, a first portion may consist of a low securement strength adhesive, such as a silicone gel, and a second portion may consist of a higher securement strength adhesive, such as a high peel strength acrylic.

Figure 10F:
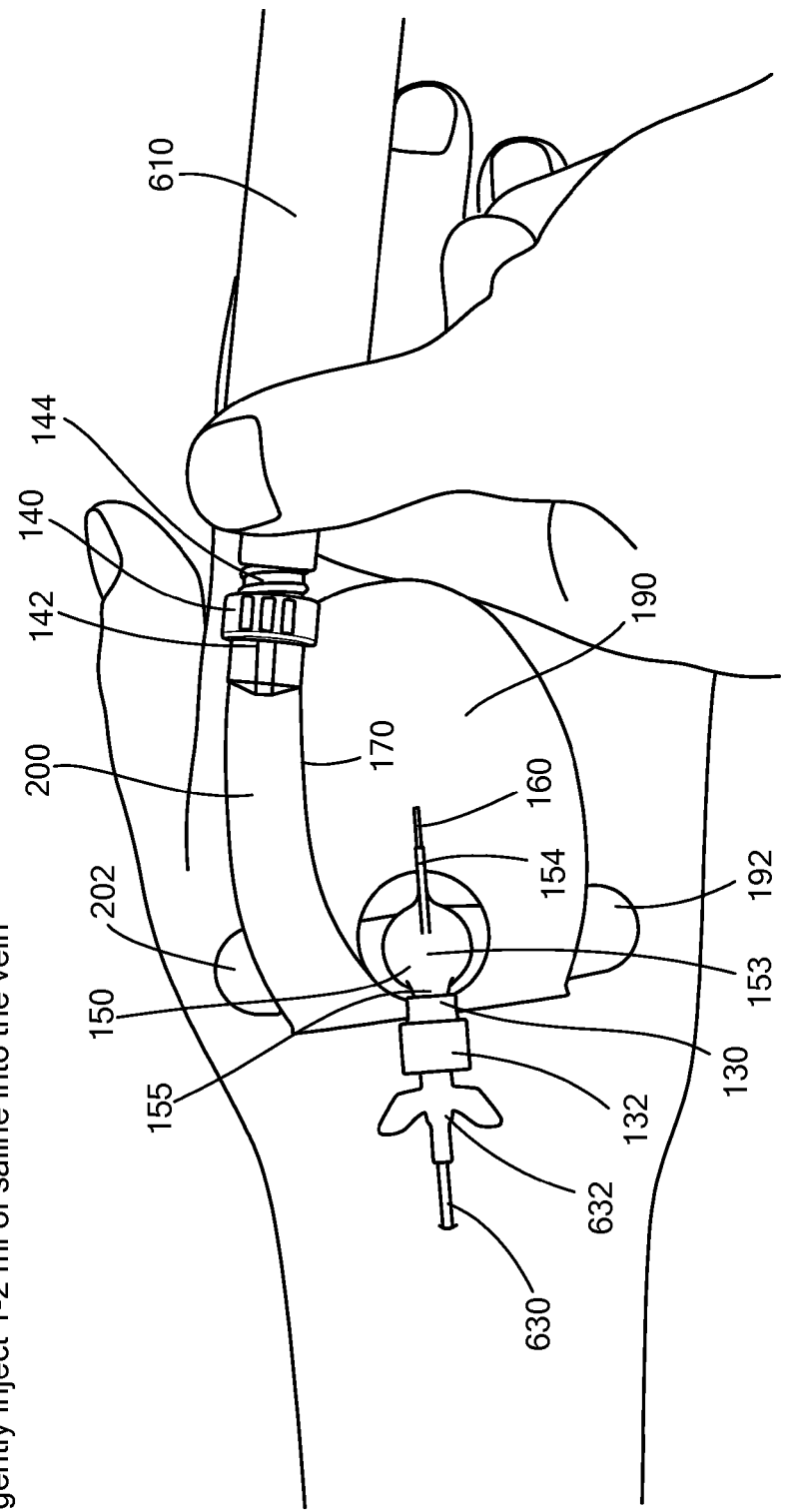

Once the docking pod 150 is adhered to the patient, it is desirable to check that the fluid flow through the stabilization device 100 and in the vein is acceptable/adequate (Step 430; FIG. 10F). To that end, the user may gently inject 1-2 ml of saline into the vein to confirm adequate fluid flow. If the fluid flow is not adequate, the user may adjust the positioning of the catheter 630 within the vein by gently lifting the docking pod 150 to release the docking pod 150 from the patient's skin, and move the catheter 630 forward into the vein while gently injecting another 1-2 ml of saline solution (Step 435). Once the flow is adequate, the user may, once again, secure the docking pod 150 to the patient's skin (Step 440).

Figure 10G:
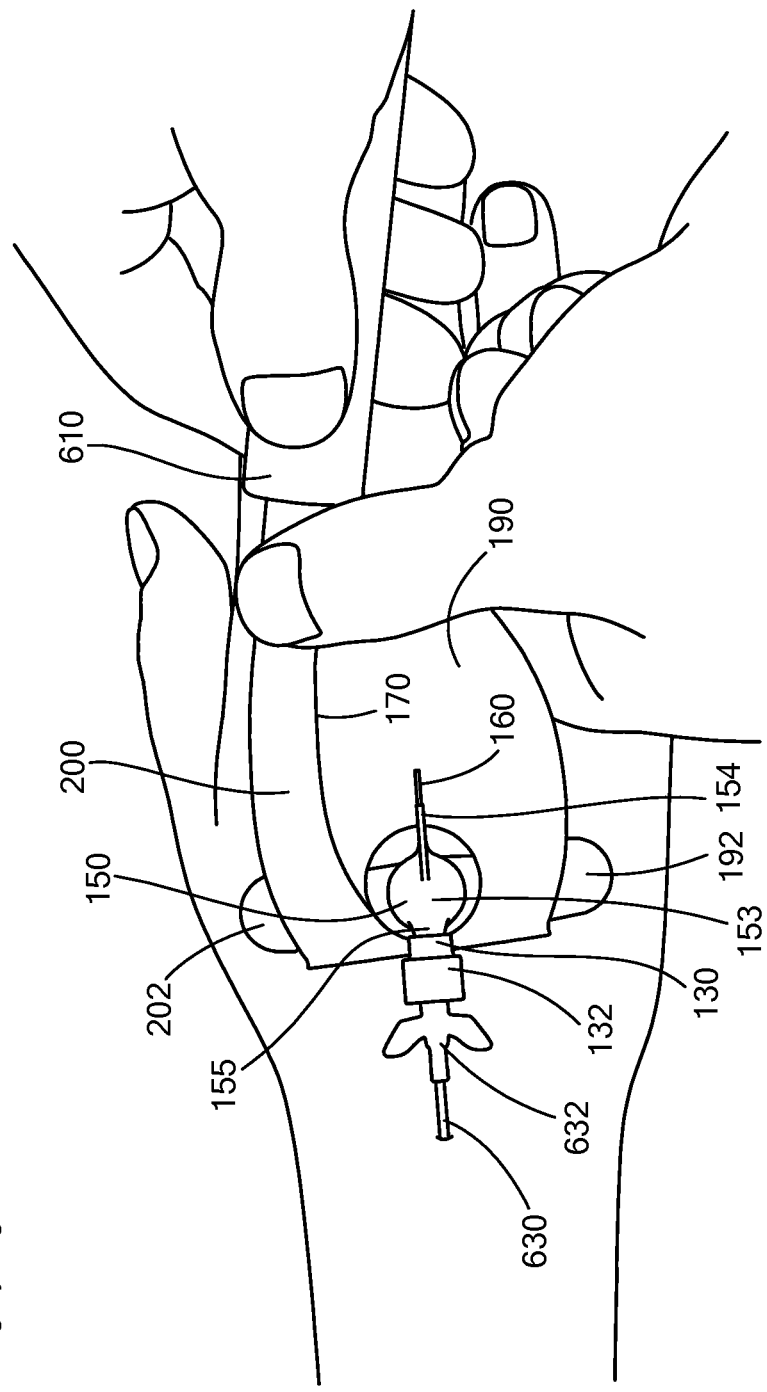
Figure 10H:
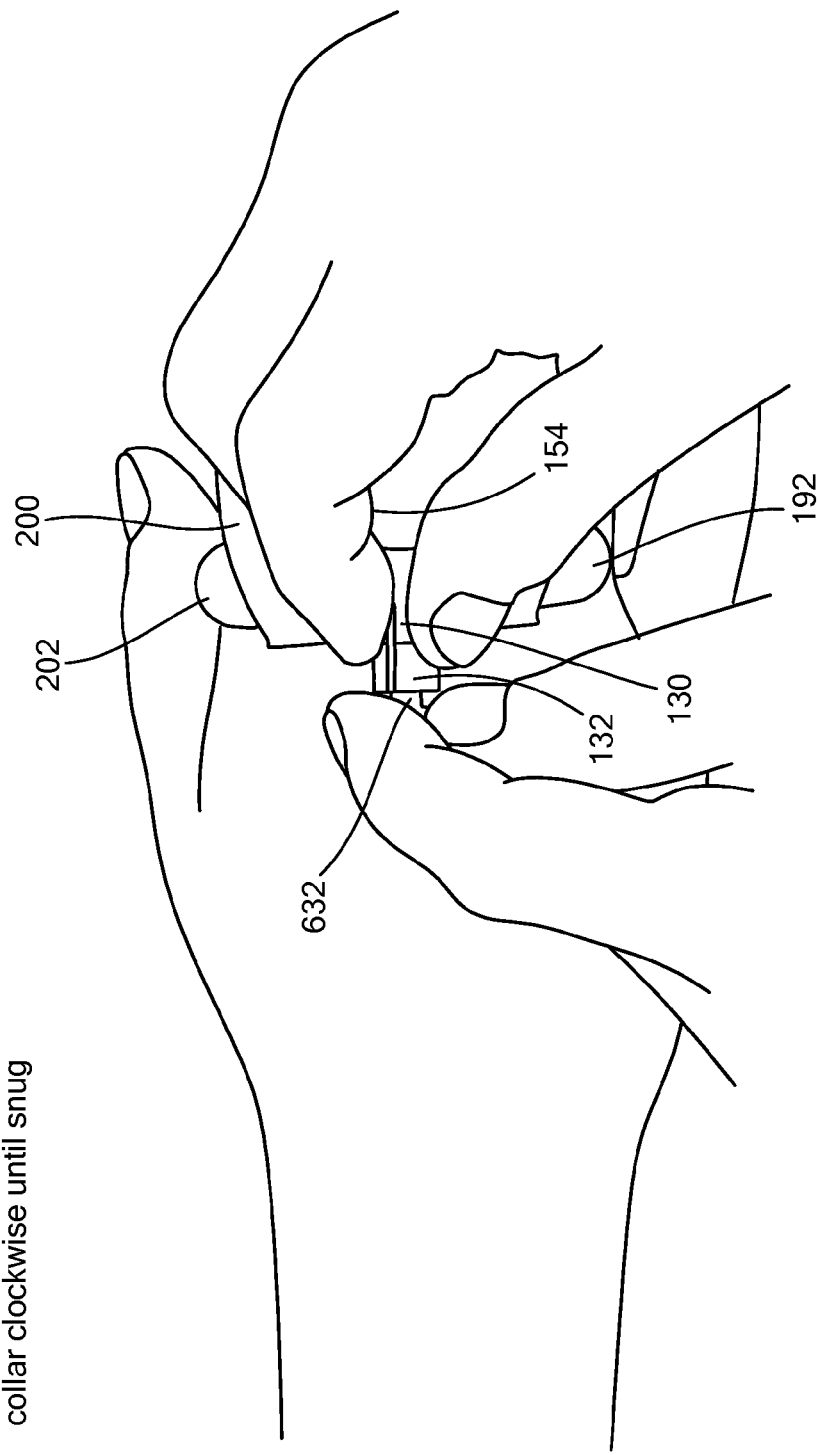

After the docking pod 150 is secured (or re-secured) and there is adequate flow within the vein, the user may disconnect the medical implement 610 from the valve 140 (Step 445; FIG. 10G), and tighten the luer connector 130 by turning the lock collar 132 (Step 450; FIG. 10H). To disconnect the medical implement 610, the user may grasp the valve 140 and turn the medical implement 610 counter-clockwise. As mentioned above, depending on the type of valve 140 used, disconnection of the medical implement 610 may decrease the pressure/create a vacuum within the fluid pathway 120 and the fluid pathway 120 may decrease in volume to compensate for the pressure change. To tighten the luer connector 130, the user may grasp the catheter hub 632 (best shown in FIGS. 10E-G) and turn a locking collar 132 on the male luer connector 130 clockwise until snug.

Figure 10I:
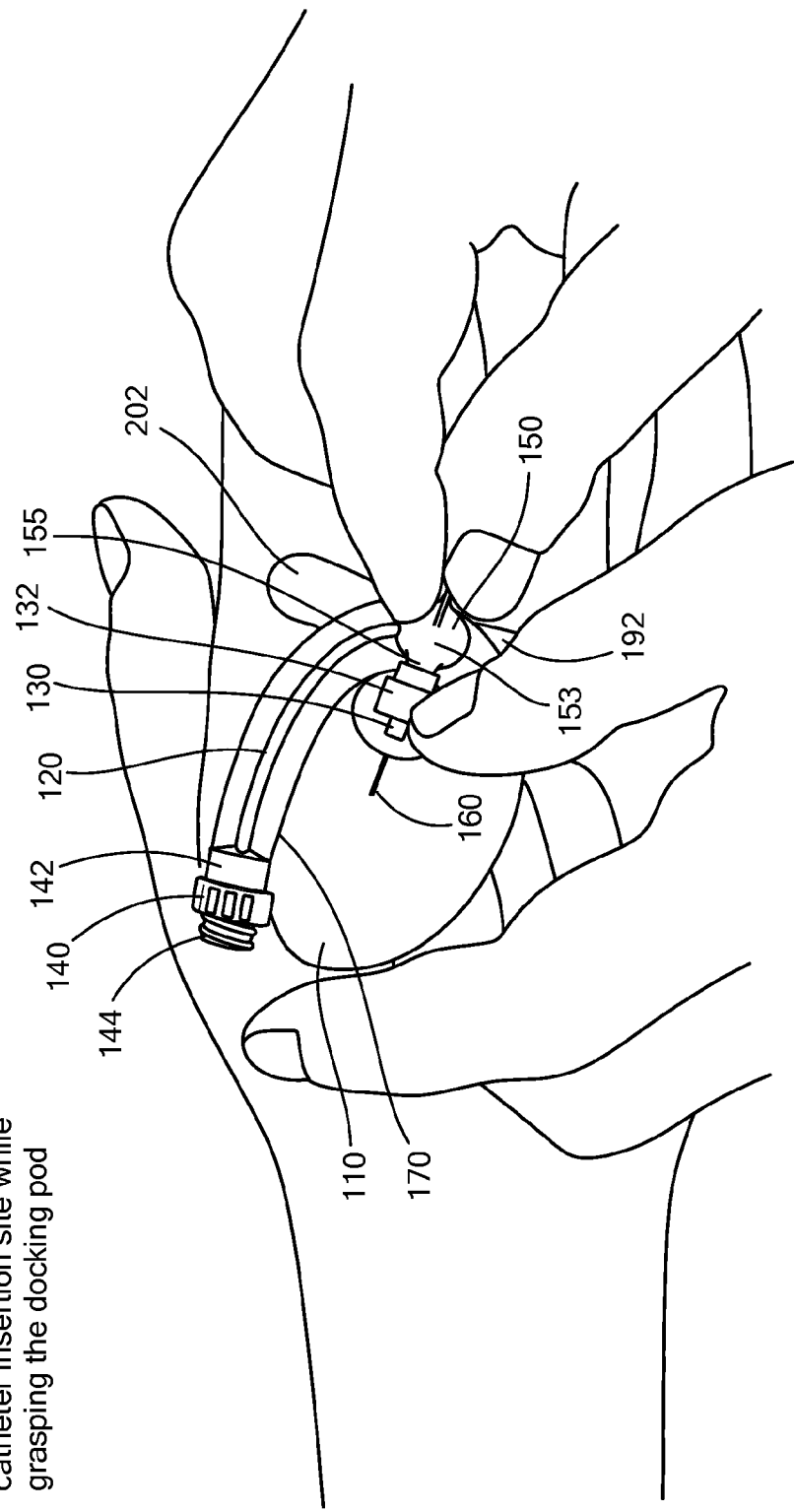

Once the medical implement 610 is disconnected and the male luer connector 130 is tightened, the user may then secure the dressing portion 110 to the patient (Step 455, FIGS. 10I-10L). As mentioned above, in some embodiments, the dressing portion 110 may be folded over during connection of the male luer connector 130 to the catheter 630. In such embodiments, to secure the dressing portion 110 to the patient, the user may flip the dressing portion 110 back over and unfold the stabilization device 100 such that it encompasses the catheter insertion site (FIG. 10I). To maintain control over and manipulate the stabilization device 100, the user may grasp the docking pod 150 and/or the grasping fin 154.

Figure 10J:
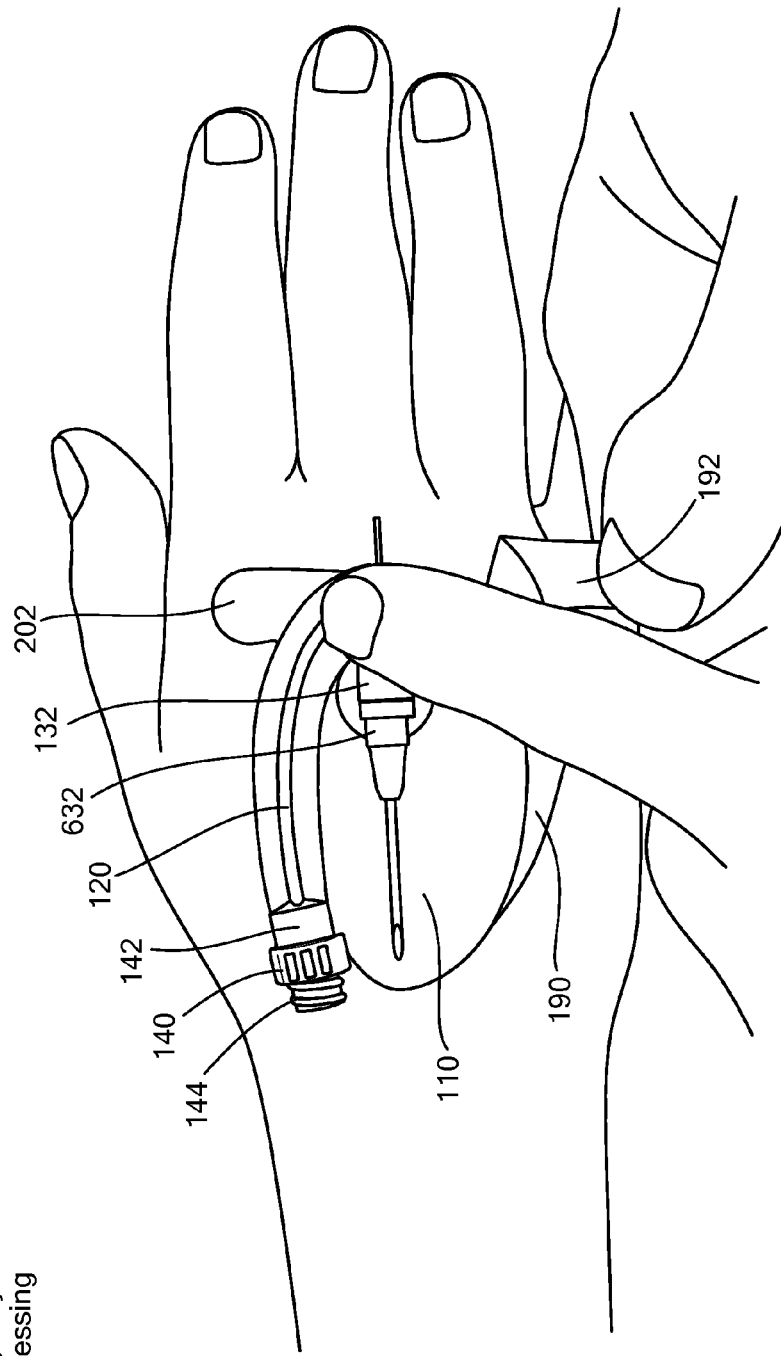
Figure 10L:
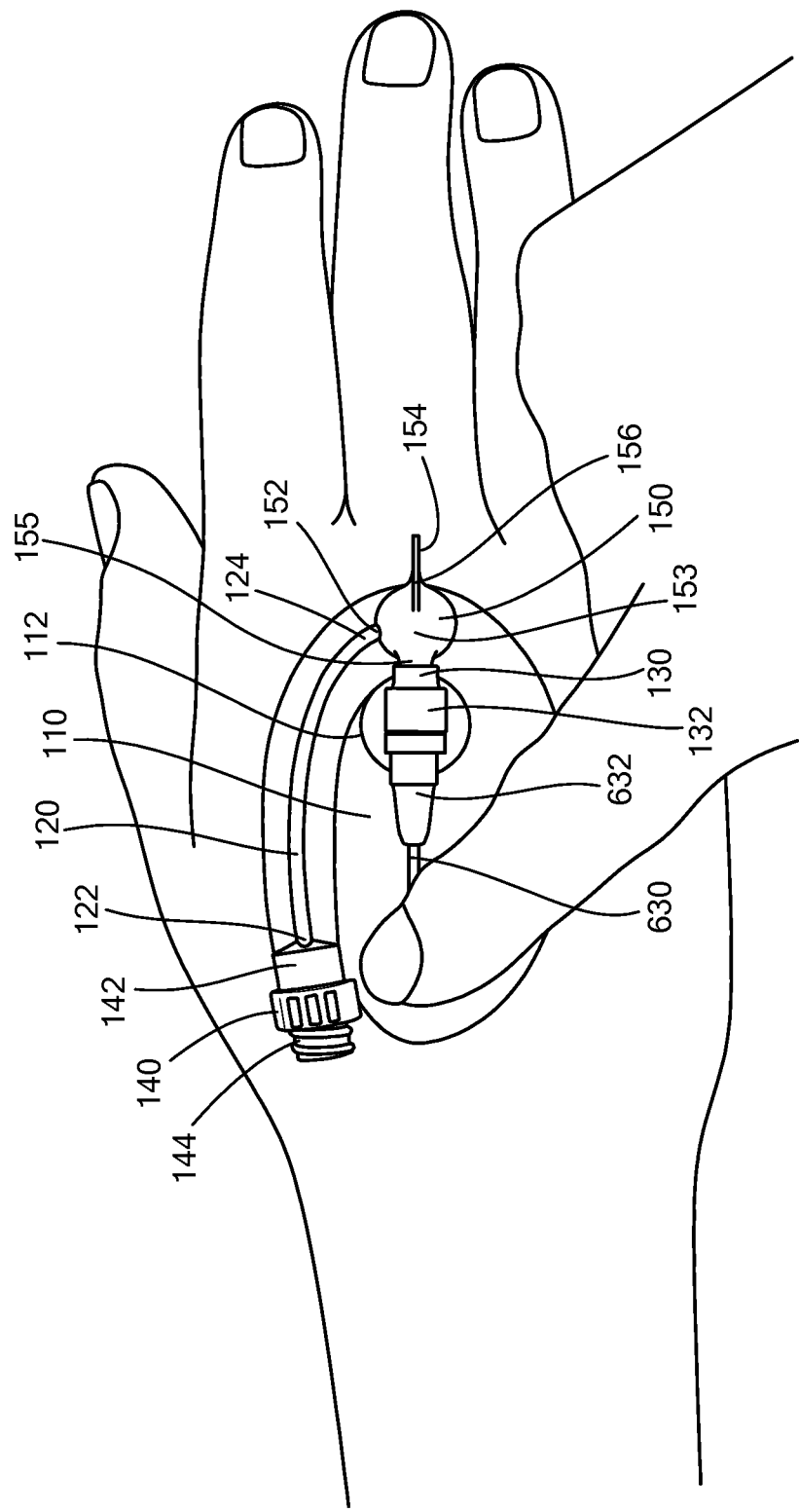

To begin securing the dressing portion 110 to the patient, the user may remove the dressing liner 190 (e.g., by pulling the dressing liner tab 192) while applying a slight pressure on the docking pod 150. The user may then gently rub down all sections of the dressing portion 110 to secure the dressing portion 110 to the patient's skin (FIG. 10J). Similarly, the user can also remove the fluid pathway liner 200 (e.g., by pulling the fluid pathway liner tab 202) while applying a slight pressure on the docking pod 150, and rubbing the fluid pathway 120 surface to secure the fluid pathway area to the patient's skin (FIG. 10K). The user may then re-rub all adhesive areas to ensure all of the adhesive areas are fully adhered to the patient (FIG. 10L). If desired, the user may then attach/secure additional dressings to the patient to further cover the insertion site and stabilize the catheter 630.

Once the stabilization device 100 is fully secured to the patient, the catheter 630 cannot be inadvertently moved. Additionally, the medical implement 610 (e.g., the syringe) may be connected and disconnected as needed without impacting the placement/location of the catheter 630 and/or kinking the fluid pathway 120. This, in turn, helps to prevent injury to the patient and ensures that adequate fluid flow through the stabilization device 100, catheter 630, and vein is maintained. Furthermore, because the stabilization device 100 includes a medical valve 140, the medical implement 610 can be easily re-attached to the stabilization device 100 at a later time to introduce fluids into the patient and/or withdraw fluids from the patient.

As mentioned above, the docking pod 150 may include adhesive located on the underside of the body 153 to allow the docking pod 150 to be secured to the patient. To that end, some embodiments may not utilize the dressing portion 110 discussed above. For example, the stabilization device may include the docking pod 150, the valve mechanism 157 within the interior of the docking pod 150, and the male luer connector 130. In such embodiments, the docking pod 150 may act as a securement/stabilization device and may be secured to the patient, and the male luer connector 130 may be connected to the outlet of the docking pod 150 (or the male luer connector 130 may be integral with the docking pod 150) and the catheter. To transfer fluid into or out of the patient, a medical implement (e.g., a syringe, male luer, etc.) may be fluidly connected to the inlet of the docking pod 150 (e.g., either directly or via a section of tubing) and used to draw fluid from the patient or deliver fluid to the patient.

It is important to note that because various embodiments of the present invention encompass the catheter insertion site and secure the catheter 630 in place, some embodiments of the present invention are able to minimize bio-burden concerns, reduce the frequency of site infection (or other complication such as infiltration), reduce catheter related blood stream infections, and reduce clinical variation.

Additionally, embodiments of the present invention have numerous advantages/benefits over prior art catheter stabilization device and techniques. For example, the above described embodiments are significantly easier to apply and provide superior catheter stabilization. Furthermore, some embodiments of the present invention eliminate the undesirable tube kinking and re-taping associated with prior art extension sets that must be intermittently pulled against the catheter hub (e.g., because of improper placement).

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A device for stabilizing a patient catheter, the device comprising:
    a docking pod having a body, an inlet, an outlet, an internal fluid path between the inlet and the outlet, and a securement surface located on an underside of the docking pod;
    a docking pod adhesive layer located at least partially on the securement surface of the docking pod, the docking pod adhesive layer configured to secure the docking pod to the patient, at least a portion of the securement surface and the docking pod adhesive layer forming a generally planar or concave surface when secured to the patient;
    a luer connector fluidly connected to the outlet of the docking pod and extending along a first longitudinal axis, the luer connector configured to be connected to the catheter; and
    a grasping element extending at least partially from the docking pod and along a second longitudinal axis, the second longitudinal axis being substantially parallel to the first longitudinal axis, the grasping element configured to provide a surface for grasping and manipulating the docking pod.

2. A device according to claim 1, further comprising:
    a valve mechanism located within the internal fluid path of the docking pod and configured to control fluid flow through the docking pod, wherein the valve mechanism is a pressure activated valve.

3. A device according to claim 2, wherein the pressure activated valve includes a diaphragm having a slit therethrough, the slit having a cracking pressure above which the slit opens to allow fluid flow through the pressure activated valve.

4. A device according to claim 3, wherein the proximally-directed cracking pressure is greater than a venous pressure of a vein in which the catheter is inserted.

5. A device according to claim 1, wherein the generally planar or concave surface stabilizes the device on the patient.

6. A device according to claim 1, wherein the grasping element is a fin.

7. A device according to claim 6 wherein the fin is movable relative to the body of the docking pod.

8. A device according to claim 1, wherein the docking pod adhesive layer and/or securement surface is configured to deform to the patient to create the generally planar or concave surface.

9. A method for stabilizing a patient catheter comprising:
providing a catheter stabilization device comprising:
a docking pod having a body, an inlet, an outlet, an internal fluid path between the inlet and the outlet, and a securement surface located on an underside of the docking pod;
a docking pod adhesive layer located at least partially on the securement surface of the docking pod, the docking pod adhesive layer configured to secure the docking pod to the patient;
a luer connector fluidly connected to the outlet of the docking pod and extending along a first longitudinal axis, the luer connector configured to be connected to the catheter; and
a grasping element extending at least partially from the docking pod and along a second longitudinal axis, the second longitudinal axis being substantially parallel to the first longitudinal axis, the grasping element configured to provide a surface for grasping and manipulating the docking pod;
connecting the catheter to the luer connector; and
adhering at least a portion of the securement surface of the docking pod to the patient via the adhesive layer to secure the docking pod to the patient and stabilize the catheter, the securement surface and the docking pod adhesive layer forming a generally planar surface or concave surface when secured to the patient.

10. A method according to claim 9, wherein the catheter stabilization device further includes:
a valve mechanism located within the internal fluid path of the docking pod and configured to control fluid flow through the docking pod, wherein the valve mechanism is a pressure activated valve.

11. A method according to claim 10, wherein the pressure activated valve includes a diaphragm having a slit therethrough, the slit having a cracking pressure above which the slit opens to allow fluid flow through the pressure activated valve.

12. A method according to claim 11, wherein the proximally-directed cracking pressure is greater than a venous pressure of a vein in which the catheter is inserted.

13. A method according to claim 9, wherein the generally planar or concave surface stabilizes the device on the patient.

14. A method according to claim 9, wherein the grasping element is a fin.

15. A method according to claim 14 wherein the fin is movable relative to the body of the docking pod.

16. A method according to claim 9, wherein adhering the securement surface to the patient causes the docking pod adhesive layer and/or securement surface to deform to the patient to create the generally planar or concave surface.

17. A device for stabilizing a patient catheter, the device comprising:
a docking means having a body, an inlet, an outlet, an internal fluid path between the inlet and the outlet, and a securement surface located on an underside of the docking means;
a securement means for securing the docking means to the patient, the securement means located at least partially on the securement surface of the docking means, the securement surface and the securement means forming a generally planar or concave surface when secured to the patient;
a connection means for connecting the catheter to the docking means, the connection means fluidly connected to the outlet of the docking means and extending a first longitudinal axis; and
a grasping means extending at least partially from the docking pod and along a second longitudinal axis, the second longitudinal axis being substantially parallel to the first longitudinal axis, the grasping means configured to provide a surface for grasping and manipulating the docking pod.

18. A device according to claim 17, further comprising:
a means for controlling fluid flow through the docking means and located within the internal fluid path, wherein the means for controlling fluid flow is pressure activated.

19. A device according to claim 18, wherein the means for controlling fluid flow includes a diaphragm having a slit therethrough, the slit having a cracking pressure above which the slit opens to allow fluid flow through the pressure activated valve.

20. A device according to claim 19, wherein the proximally-directed cracking pressure is greater than a venous pressure of a vein in which the catheter is inserted.

21. A device according to claim 17, wherein the generally planar or concave surface stabilizes the device on the patient.

22. A device according to claim 17 wherein the grasping means is movable relative to the body of the docking means.

23. A device according to claim 17, wherein the securement means and/or securement surface are configured to deform to the patient to create the generally planar or concave surface.

24. A device for stabilizing a patient catheter, the device comprising:
a docking pod having a body, an inlet, an outlet, an internal fluid path between the inlet and the outlet, and a securement surface located on an underside of the docking pod;
a docking pod adhesive layer located at least partially on the securement surface of the docking pod, the docking pod adhesive layer configured to secure the docking pod to the patient;
a luer connector fluidly connected to the outlet of the docking pod and extending along a first longitudinal axis, the luer connector configured to be connected to the catheter; and
a fin extending off a surface of the docking pod and along a second longitudinal axis and configured to provide a surface for grasping and manipulating the docking pod, the second longitudinal axis being substantially parallel to the first longitudinal axis.

25. A device according to claim 24, further comprising:
a pressure activated valve mechanism located within the internal fluid path of the docking pod and configured to control fluid flow through the docking pod, wherein the pressure activated valve mechanism includes a diaphragm having a slit therethrough, the slit having a cracking pressure above which the slit opens to allow fluid flow through the pressure activated valve.

26. A device according to claim 25, wherein the proximally-directed cracking pressure is greater than a venous pressure of a vein in which the catheter is inserted.

27. A device according to claim 24 wherein the fin is movable relative to the body of the docking pod.

28. A device according to claim 27, wherein the fin is secured to the docking pod via a living hinge.

29. A device according to claim 24, wherein the fin is releasably secured to the body of the docking pod.

* * * * *

UNITED STATES PATENT AND TRADEMARK OFFICE
CERTIFICATE OF CORRECTION

PATENT NO.        : 9,545,502 B2                                       Page 1 of 1
APPLICATION NO.   : 14/802270
DATED             : January 17, 2017
INVENTOR(S)       : Luis Maseda et al.

It is certified that error appears in the above-identified patent and that said Letters Patent is hereby corrected as shown below:

In the Claims

In Column 20, Line 20:
replace "a first longitudinal axis; and"
with "along a first longitudinal axis; and"

Signed and Sealed this
Eleventh Day of April, 2017

Michelle K. Lee
*Director of the United States Patent and Trademark Office*